US011491483B2

(12) United States Patent
Lee et al.

(10) Patent No.: US 11,491,483 B2
(45) Date of Patent: Nov. 8, 2022

(54) MICROFLUIDIC DEVICES AND METHODS FOR HIGH THROUGHPUT ELECTROPORATION

(71) Applicant: Ohio State Innovation Foundation, Columbus, OH (US)

(72) Inventors: L. James Lee, Columbus, OH (US); Junfeng Shi, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 35 days.

(21) Appl. No.: 16/276,973

(22) Filed: Feb. 15, 2019

(65) Prior Publication Data
US 2019/0247852 A1    Aug. 15, 2019

Related U.S. Application Data

(60) Provisional application No. 62/631,251, filed on Feb. 15, 2018.

(51) Int. Cl.
*B01L 3/00*      (2006.01)
*C12N 15/87*     (2006.01)
(Continued)

(52) U.S. Cl.
CPC ... *B01L 3/502715* (2013.01); *B01L 3/502761* (2013.01); *C12M 35/02* (2013.01);
(Continued)

(58) Field of Classification Search
None
See application file for complete search history.

(56) References Cited

U.S. PATENT DOCUMENTS 7,338,796 B1    3/2008  Davalos et al.
8,524,679 B2    9/2013  Pachuck
(Continued)

FOREIGN PATENT DOCUMENTS

CN    101044251 A    9/2007
CN    101201350 A    6/2008
(Continued)

OTHER PUBLICATIONS

OSU Libray Catalog, online cite of Shi, Shi, Junfeng, Development of nanoelectroporation-based biochips for living cell interrogation and extracellular vesicle engineering / by Junfeng Shi Imprint [Columbus] : Ohio State University, 2017 and Frequently asked questions. 2 pages. (Retrieved Dec. 4, 2020) (Year: 2020).*
(Continued)

*Primary Examiner* — William H. Beisner
(74) *Attorney, Agent, or Firm* — Meunier Carlin & Curfman LLC

(57) ABSTRACT

Devices for high throughput cell electroporation include a trapping component that at least partially defines an upper boundary of a microfluidic chamber. A cell trap array is patterned on the underside of the trapping component, and a channeling component is positioned beneath the trapping component. The channeling component includes a vertically oriented nanochannel array. The trapping component and the channeling component are positioned such that a given nanochannels is positioned beneath a cell trap. During use, fluid flow holds trapped cells in secure contact with the nanochannels beneath the cell trap. The device further includes upper and lower electrode layers for generating an electric field to electroporate trapped cells via the nanochannel array. A reservoir positioned beneath the channeling component can be filled transfection reagent solution. During electroporation, the transfection reagent solution travels
(Continued)

through the nanochannel array during to transfect the trapped cells.

26 Claims, 21 Drawing Sheets

(51) Int. Cl.
    *C12N 13/00* (2006.01)
    *C12M 1/42* (2006.01)
(52) U.S. Cl.
    CPC .............. *C12N 13/00* (2013.01); *C12N 15/87* (2013.01); *B01L 2200/025* (2013.01); *B01L 2200/0668* (2013.01)

(56) References Cited

U.S. PATENT DOCUMENTS

| | | | |
|---|---|---|---|
| 9,816,086 | B2 | 11/2017 | Lee et al. |
| 2010/0003666 | A1 | 1/2010 | Lee et al. |
| 2011/0059867 | A1 | 3/2011 | Kim et al. |
| 2012/0004144 | A1 | 1/2012 | Perroud et al. |
| 2014/0134263 | A1 | 5/2014 | Wu et al. |
| 2014/0256047 | A1 | 9/2014 | Lee et al. |
| 2015/0018226 | A1* | 1/2015 | Hansen ................ G01N 33/569 506/9 |
| 2016/0257918 | A1 | 9/2016 | Chapman et al. |
| 2020/0047182 | A1* | 2/2020 | Meldrum .......... B01L 3/502761 |

FOREIGN PATENT DOCUMENTS

| | | |
|---|---|---|
| CN | 101981447 A | 2/2011 |
| CN | 102186992 A | 9/2011 |
| CN | 103998932 A | 8/2014 |
| CN | 103197066 B | 12/2015 |
| WO | 20091002783 | 8/2009 |
| WO | 2016168492 A1 | 10/2016 |
| WO | 2017054086 A1 | 4/2017 |
| WO | 2018119091 A1 | 6/2018 |
| WO | 2019028450 A1 | 2/2019 |

OTHER PUBLICATIONS

International Search Report and Written Opinion issued for Application No. PCT/US2019/018164, dated Apr. 15, 2019, 9 pages.
Shi, et al., Development of Nanoelectroporation-based Biochips for Living Cell Interrogation and Extracellular Vesicle Engineering, Dissertation Submitted to the Graduate School of The Ohio State University. 2017. [retrieved on Mar. 20, 2019]. Retrievd from the internet: <URL: https://etd.ohiolink.edu/!etd.send_file?accession=osu1503059915552435> pp. 72, 74, 82-84, 104-105.
Boukany, et al., (2011). Nanochannel electroporation delivers precise amounts of biomolecules into living cells. Nat Nanotechnol, 6(11), 747-754. doi:10.1038/nnano.2011.164.
Chang, et al., (2016). 3D nanochannel electroporation for high-throughput cell transfection with high uniformity and dosage control. Nanoscale, 8(1), 243-252. doi:10.1039/c5nr03187g.
Chang, et al., (2016). Controllable Large-Scale Transfection of Primary Mammalian Cardiomyocytes on a Nanochannel Array Platform. Small, 12(43), 5971-5980. doi:10.1002/smll.201601465.
Chang, et al., (2015). Dielectrophoresis-assisted 3D nanoelectroporation for non-viral cell transfection in adoptive immunotherapy. Lab Chip, 15(15), 3147-3153. doi:10.1039/c5lc00553a.
Chang, et al., (2015). Magnetic tweezers-based 3D microchannel electroporation for high-throughput gene transfection in living cells. Small, 11(15), 1818-1828. doi:10.1002/smll.201402564.
Di Carlo, et al., (2006). Single-cell enzyme concentrations, kinetics, and inhibition analysis using high-density hydrodynamic cell isolation arrays. Anal Chem, 78(14), 4925-4930. doi:10.1021/ac060541s.
Skelley, et al. (2009). Microfluidic control of cell pairing and fusion. Nat Methods, 6(2), 147-152. doi:10.1038/nmeth.1290.
Zhang, et al., (2014). Block-Cell-Printing for live single-cell printing. Proc Natl Acad Sci U S A, 111(8), 2948-2953. doi:10.1073/pnas.1313661111.
Daniel Gallego-Perez, et al., "Topical tissue nano-transfection mediates non-viral stroma reprogramming and rescue", Nature Nanotechnology, vol. 12, 2017, pp. 974-979.
Extended European Search Report, issued for Application No. 19755136.9, dated Nov. 8, 2021.
Chang, Lingqian, et al. "3D nanochannel electroporation for high-throughput cell transfection with high uniformity and dosage control." Nanoscale 8.1 (2016): 243-252.
Kanuma, Tomohiro, et al. "CD63-mediated antigen delivery into extracellular vesicles via DNA vaccination results in robust CD8+ T cell responses." The Journal of Immunology 198.12 (2017): 4707-4715.
Khine, Michelle, et al. "A single cell electroporation chip." Lab on a Chip 5.1 (2005): 38-43.
McKnight, Timothy E., et al. "Tracking gene expression after DNA delivery using spatially indexed nanofiber arrays." Nano Letters 4.7 (2004): 1213-1219.
Mizrak, Arda, et al. "Genetically engineered microvesicles carrying suicide mRNA/protein inhibit schwannoma tumor growth." Molecular Therapy 21.1 (2013): 101-108.
Shi, Junfeng, Development of Nanoelectroporation-based Biochips for Living Cell Interrogation and Extracellular Vesicle Engineering, Thesis, May 10, 2017, pp. 130-136.

* cited by examiner

MICROFLUIDIC DEVICES AND METHODS FOR HIGH THROUGHPUT ELECTROPORATION

RELATED APPLICATIONS

This application claims priority to U.S. Provisional Application Ser. No. 62/631,251, filed Feb. 15, 2018, which is hereby incorporated by reference in its entirety.

FIELD

The invention is directed to high throughput electroporation of cells, and more specifically, to the use of microfluidic devices to perform the same.

BACKGROUND

Efficient intracellular delivery of exogenous materials (e.g. nucleic acids, proteins, drugs, molecular probes, nanodevices, etc.) plays a key role in a diversity of biomedical and pharmaceutical applications ranging from gene editing, cell-based therapy, regenerative medicine, production of therapeutic molecules by cell-based bioreactors, to fundamental biology research probing molecular mechanism in diseases such as cancer. Precise, rapid and benign introduction of biomolecules into a large population of cells at single cell resolution has thus long fascinated the scientific community. To circumvent the safety concerns raised by viral vectors, a variety of non-viral delivery approaches have been developed, including chemical carrier-mediated methods (e.g., synthetic lipoplex and polyplex nanocarriers, uptaken by cells via endocytosis and endosomal escape and physical membrane-penetrating methods (such as micro-injection, biolistic gene gun, laser irradiation, and sonoporation). Electroporation has been a popular physical delivery method since its invention. Conventional bulk electroporation (BEP) is the commercially available system in which a mixed conductive buffer containing both suspended cells and transfection reagents is loaded into the electroporation cuvette with anode and cathode from two ends that apply high-voltage electric pulses (>1000 V) to facilitate cargo delivery in permeabilized cells. While BEP offers the advantage of simplicity to use without any package of delivery materials, it suffers from low cell viability and significant cell-to-cell variation owing to the non-uniform electric field imposed on the large number of cells randomly suspended in the cuvette.

A rapid growth of miniaturized versions of electroporation integrated in microfluidics-enabled lab-on-a-chip platforms has been witnessed since 2000. Microscale-electroporation (MEP), which confines the electric field to the scale of the cell, allows for a fine control over cell poration condition, i.e. creating a more uniform porating electric field by applying a significantly lower voltage (<10 V) which minimizes cell death. However, in both BEP and MEP, the process of cargo delivery is diffusion/endocytosis-based, which is essentially stochastic.

SUMMARY

The microfluidic device for high throughput cell electroporation described herein is based on nanoelectroporation (NEP) and offers high yield, high throughput NEP-based intracellular delivery. The device facilitates rapid cell loading, large-scale and uniform NEP with single-cell resolution that eliminates the stochastic effects of BEP and MEP techniques. The same platform further enables fast post-transfection cell collection. Unlike optic and electromagnetic cell trapping techniques (e.g., optical tweezers, magnetic tweezers, DEP) that require either cumbersome instrumental setup and calibration procedures, or rely heavily on the expertise and/or experience of users, this microfluidic cell manipulation approach is easy to implement, cell-friendly, and also highly efficient.

The devices disclosed herein include a trapping component that at least partially defines an upper boundary of a fluidic chamber. The trapping component includes a cell trap array, and each cell trap of the cell trap array extends downward into the fluidic chamber. The devices further include a channeling component that is positioned beneath the trapping component. The channeling component at least partially defines a lower boundary of the fluidic chamber. The channeling component includes a nanochannel array in fluid communication with and extending downward from the fluidic chamber. A plurality of the nanochannels of the nanochannel array are positioned in vertical alignment with a plurality of cell traps of the cell trap array. The devices further include upper and lower electrode layers for generating an electric field within the fluidic chamber.

Some embodiments of the devices disclosed herein may also include a reservoir positioned beneath the channeling component. The upper boundary of the reservoir is at least partially defined by the channeling component, such that the reservoir is in fluid communication with the fluidic chamber. The lower boundary of the reservoir can be at least partially defined by the lower electrode. In some embodiments, the side boundaries of the reservoir can be at least partially defined by a spacing material.

As noted above, the channeling component includes a nanochannel array. In some embodiments, one or more nanochannels of the nanochannel array can have a height of from 1 micrometer to 20 micrometers, and one or more nanochannels of the nanochannel array can have a diameter of from 1 nanometer to 999 nanometers. The channeling component can also include a plurality of microchannels extending upward from a lower surface. Each microchannel can be in fluid communication with multiple nanochannels of the nanochannel array.

As noted above, the trapping component includes a cell trap array. Each cell trap of the cell trap array can include a cupping region partially defined by walls of the cell trap. The cupping region can include an entry portion oriented toward the inlet side of the fluidic chamber. In some embodiments, a space exists between the lower edge of each cell trap and the channeling component. The plurality of nanochannels of the nanochannel array are each positioned vertically beneath the cupping region of a cell trap.

The upper and lower electrode layers are configured to generate an electric field within the fluidic chamber. The upper electrode layer can be positioned, for example, on a lower surface of the trapping component and in fluid communication with the fluidic chamber. The lower electrode can be positioned, for example, beneath the channeling component and in fluid communication with the fluidic chamber.

Methods of performing high throughput cell electroporation are also disclosed herein. The methods include flowing a cell suspension in a forward direction through an inlet and into a fluidic chamber of a microfluidic device, trapping a plurality of cells within an array of cell traps in the fluidic chamber, and continuing a forward flow of fluid from the inlet of the fluidic chamber to the outlet of the fluidic chamber, thereby creating fluidic patterns around the cell traps that position at least a portion of the trapped cells into secure contact with nanochannels of the nanochannel array. The method further includes electroporating the portion of the trapped cells that are in secure contact with the nanochannels, releasing the electroporated cells from the cell traps, and collecting the electroporated cells.

In some embodiments of the method, the cell suspension has a cell density of from 3 million cells/mL to 15 million cells/mL. The cell suspension can be flowed through the inlet of the fluidic chamber at an inlet flow velocity of from 70 to 130 microns per second. During trapping and electroporation, flow within the cupping region of the cell traps is completely stopped, or slowed to no more than 20% of the inlet flow velocity.

Electroporating the portion of trapped cells can include generating an electric field within and immediately adjacent to each nanochannel. In some embodiments, the strength of the electric field within the microfluidic chamber (at a distance away from a nanochannel equivalent to the nanochannel diameter) is less than 20% the strength of the electric field within the nanochannel. In some embodiments, for time periods greater than 10 minutes, the rate of cell electroporation is greater than 1,000 cells per minute per square centimeter of microfluidic chamber.

The methods can further include transfecting at least some of the portion of trapped cells with genetic material, drugs, proteins, molecular probes, nanoparticles, and/or sensors during electroporation. In some embodiments, the cells are transfected with genetic material up to 100,000 base pairs.

In some embodiments, slowing or stopping the forward flow of fluid facilitates the release of the cells from the cell traps. In some embodiments, reversing the direction of fluid flow within the microfluidic device facilitates the release and collection of the electroporated cells.

DESCRIPTION OF DRAWINGS

The device is explained in even greater detail in the following drawings. The drawings are merely exemplary to illustrate the structure of garments and certain features that may be used singularly or in combination with other features. The drawings are not necessarily drawn to scale.

(FIG. 8A) a top-view shows model geometry (unit: μm) (FIG. 8B) 3D modelling (FIG. 8C-FIG. 8D) FEM modeling results of the flow velocity field distribution in the micro-trap cross-section in the y-z plane (FIG. 8C) and x-z plane (FIG. 8D).

(FIG. 9A) Top-view showing model geometry (unit: μm) (FIG. 9B-9C) FEM modeling results of the flow velocity field (directional arrows) and the velocity magnitude of the z component (indicated by color legend, unit: mm/s) in (FIG. 9B) y-z plane slice and (FIG. 9C) x-z plane slice.

(FIG. 11A) An exploded view of schematic of the microfluidic 3D NEP platform assembly showing the main components. (FIG. 11B-11D) Schematics of the operation flow of the microfluidic NEP device. (FIG. 11B) Cell loading: individual cells are captured in micro-traps by a hydrodynamic force. (FIG. 11C) NEP-based transfection of target molecules by applying a focused electric field through a nanochannel. (FIG. 11D) Cell collection: transfected cells can be released from cell traps and collected from the inlet of the microfluidic channel, by simply reversing the flow direction. (FIG. 11E) SEM images of the micro-fabricated cell trap array (FIG. 11F-11G) zoom-in SEM micrographs showing the detailed structure of a single cell trap. Measured cell trap geometry: 15 μm wide, 12 μm long and 15 μm in height. A designed gap in the middle of the trap to let the fluid pass through.

(FIG. 14A) Schematic of Bosch Process, deep reactive-ion etching (DRIE) progression: silicon sample is under repeated SF6-based etch step and C4F8-based passivation step. Sidewall is protected by polymeric passivation (nCF2). (FIG. 14B) SEM micrograph of the 3D silicon NEP chip cross-section showing smooth and straight channel sidewalls achieved by optimized conditions of deep reactive ion etching (DRIE) with repeated etching and passivation cycles.

(FIG. 15A-15B) A SEM picture of the top-view of a uniform nanopore array with 5 μm pitch and a zoom-in image of a single nanochannel showing φ500 nm diameter. (FIG. 15C) A cross-section image showing multiple nanochannels connected with one microchannel.

(FIG. 16A) The cell capture efficiency curve with different cell density conditions. Images taken after 2-min trapping. The flow rate was set at 100 μm/s. (FIG. 16B-16C) Fluorescence images of the cell array after microfluidic cell trapping. Scale bars: 300 μm. (FIG. 16B) A large-scale cell array showing a high trapping efficiency >90%. (FIG. 16C) A merged image (phase contrast and DAPI) showing positions of captured cells and micro-traps.

(FIG. 18B) The electric field strength distribution. An extremely high electric field strength ~20 V/μm is created within and close to the nanochannel region, which nanoporates cell membrane and drives charged biomolecules via electrophoresis. (FIG. 18C) The electric field strength drops sharply away from the nanochannel interface (red line). Nanochannel region defined $z \in (-10, 0)$.

(FIG. 19A) Suspension NK-92 cells suffered extremely low to no plasmid transfection efficiency. Only one cell showed green fluorescence indicated by the arrow. (FIG. 19B) Adherent cells could be transfected after cells attached on the NEP chip surface. But this cell anchor process took at least 4-8 h. Inset: a SEM image of a MEF cell spread on the NEP chip surface. (FIG. 19C) The transfection efficiency comparison of microfluidic cell trapping approach vs. other random cell loading methods. (FIG. 19D) The delivery dosage comparison of YOYO-1 labelled plasmids to MEF cells quantified by fluorescence imaging.

(FIG. 20A) Fluorescence micrographs of a living cell array after microfluidic cell trapping followed by NEP-based transfection of FAM-labelled ODN. Scale bar: 100 μm. (FIG. 20B) Fluorescence images of a large-scale living cell array, after NEP-based delivery of YOYO™-1 labelled DNA plasmids (7 kbp). Zoom-in images of single transfected cell located within the micro-trap. Scale bars: 300 μm (the large-scale cell array), 25 μm (single cell image)

(FIG. 23A) Fluorescence image of trapped NE array (nucleus staining in DAPI) (FIG. 23B) Merged phase contrast and fluorescence image showing uniform transfection in individual NEs. Scale bars: 25 μm (c) bar chart of transfection efficiency comparison: mNEP (~80%), centrifuge method (25%) and random loading as the control (<5%).p<0.01, *p<0.005, t-test.

DETAILED DESCRIPTION

Figure 1:
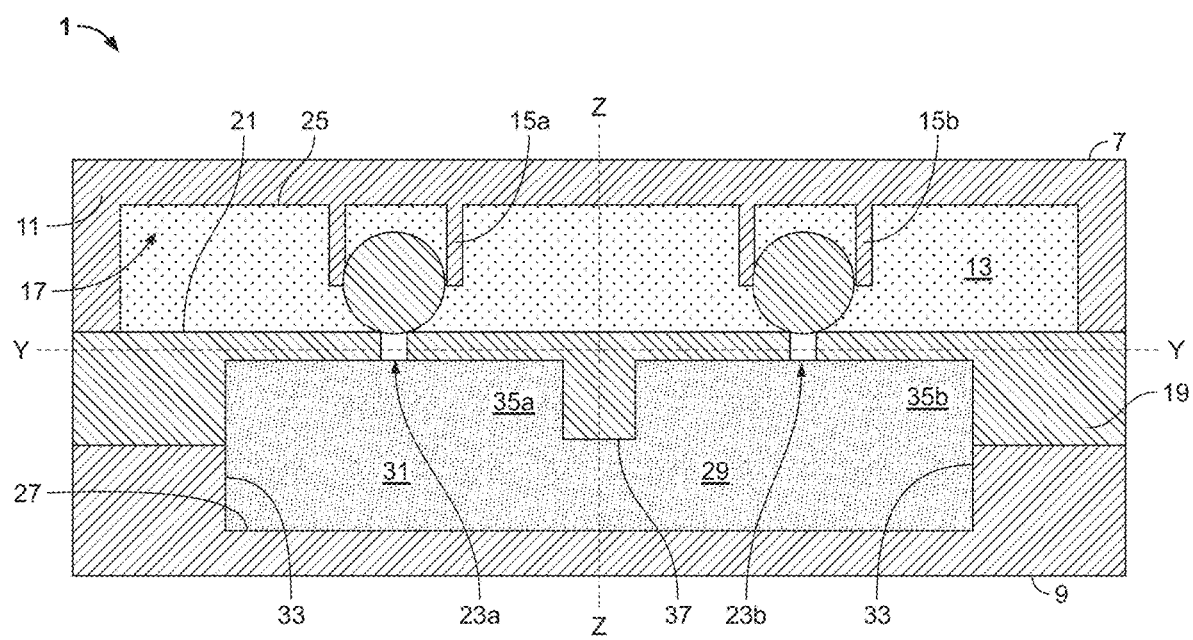
FIG. 1 is a cross sectional schematic of an embodiment of a high throughput electroporation device.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Developments in nano-electroporation (NEP) have begun to address some of the limitations seen in BEP and MEP. Boukany et al. (2011) describes an innovative NEP technology that is capable of dosage-controllable and benign intracellular delivery using electrophoresis-assisted cargo "injection" through a nanochannel aperture. Work by Chang et al., (2015, Nanoscale: 2016) seeks to address the limited throughput (i.e., <200 cells) of the Boukany system with a three-dimensional (3D) NEP platform featuring a large nanochannel array in the z-direction (Chang, Bertani, et al., 2016; Chang, Gallego-Perez, et al., 2015). The references Boukany et al., 2011, Chang et al., 2015, and Chang, Bertani et al., 2016 are hereby incorporated by reference in their entireties.

While the z-direction nanochannels can be engineered by semiconductor cleanroom-based fabrication techniques, cell manipulation (i.e., close cell contact against the nanochannel outlet), in a simple yet efficient manner, is a major technical hurdle that needs to be overcome. Since the electric field, which accelerates the charged biomolecules in the nanochannel, and porates the cell membrane during the NEP process, diminishes quickly outside the nanochannel, close contact between the to-be-electroporated cells and the corresponding nanochannels is needed. Previous cell loading techniques coupled with NEP suffered from either low throughput (e.g., single-cell manipulation by an optical tweezer), excessive cell perturbation (e.g., cell labelling with magnetic beads and then cell manipulation by a magnetic tweezer) (Chang, Howdyshell, et al., 2015), or exposure to physiologically unfavorable low-conductivity buffer in the dielectrophoresis (DEP) based cell manipulation (Chang, Gallego-Perez, et al., 2015) which would compromise cell viability. It has been previously demonstrated that hydrodynamic weir-like microstructures could successfully immobilize cells (Chang, Gallego-Perez, et al., 2016; Di Carlo, Aghdam, & Lee, 2006; Skelley, Kirak, Suh, Jaenisch, & Voldman, 2009; Zhang, Chou, Xia, Hung, & Qin, 2014), however, those devices were unable to perform high-throughput NEP applications.

The microfluidic cell-trapping and nano-electroporation (NEP) platform described herein offers high yield of NEP-based intracellular delivery (i.e., >20,000 cells per $cm^2$ within minutes) at high-throughput. The new platform allows rapid cell loading, large-scale and uniform NEP with single-cell resolution that eliminates the stochastic effects of BEP and MEP techniques. The same platform further enables fast post-transfection cell collection. Unlike optic and electromagnetic cell trapping techniques (e.g., optical tweezers, magnetic tweezers, DEP) that require either cumbersome instrumental setup and calibration procedures, or rely heavily on the expertise and/or experience of users, this microfluidic cell manipulation approach is easy to implement, cell-friendly, and also highly efficient. The precise cell positioning is achieved by a microfluidic cell trap array. By optimizing the cell density and flow rate, a capture efficiency >90% can be achieved within 2 minutes. The computational fluidic dynamics (CFD) simulation reveals that this cell trap structure slows the flow velocity within the cupping region of the cell trap to protect the trapped cells from shear stress. The structure further generates a downward flow velocity to push the trapped cell against the nanochannels on the substrate. Therefore, the platform can be used for both adherent and suspension cells, regardless of cellular anchor properties. Experimental results described in the Examples section show that the microfluidic cell trapping significantly improves the NEP-based transfection efficiency over a previous design, achieving uniform and precise delivery of various cargos including a small fluorescently-labeled oligodeoxynucleotide (ODN) and a large ~9 k bp plasmid.

Figure 2:
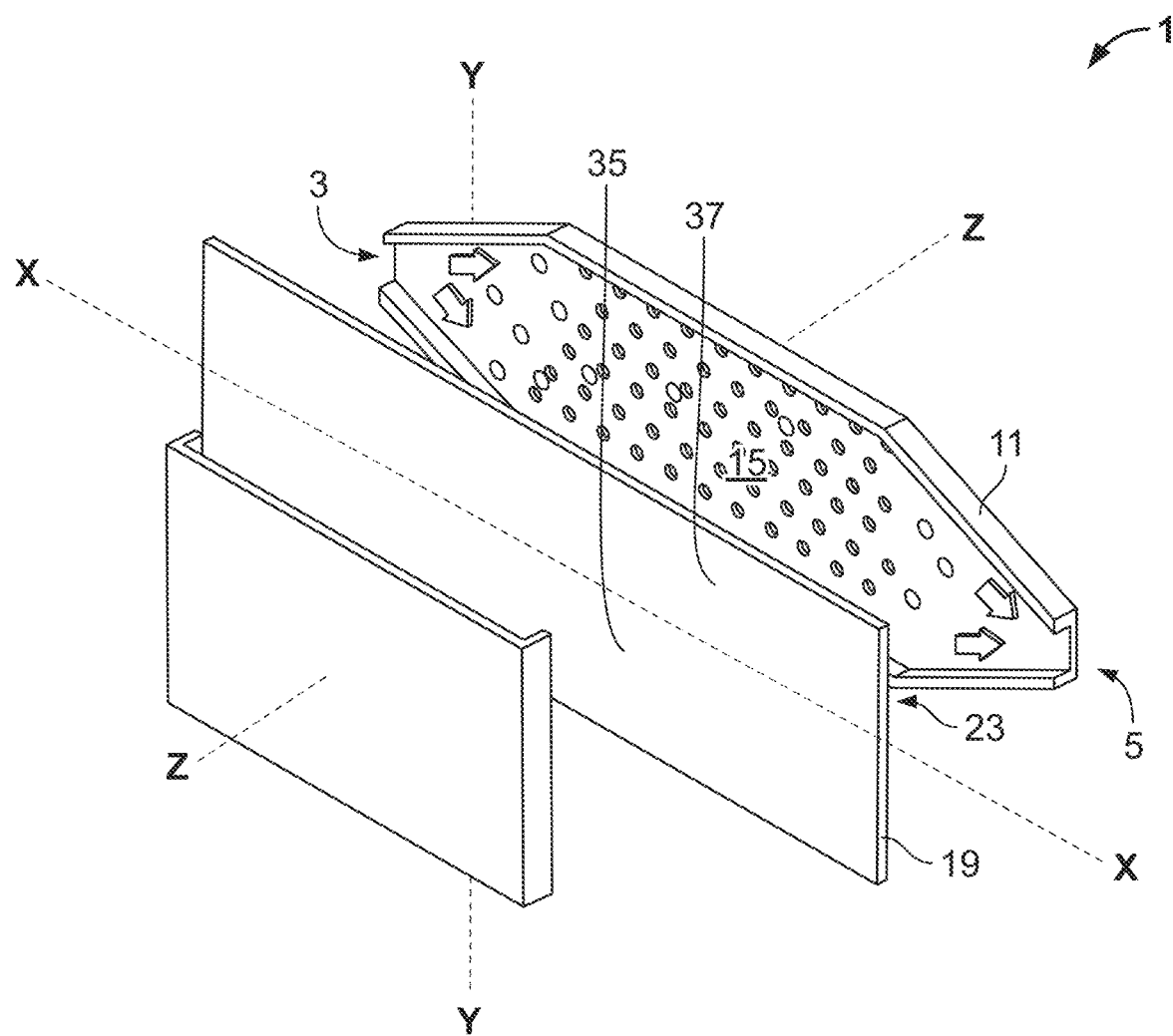
FIG. 2 is an exploded perspective view of an embodiment of a high throughput electroporation device.

A cross section of an example microfluidic device 1 for high throughput cell electroporation is shown in FIG. 1, and an exploded perspective view of certain aspects of the device 1 is shown in FIG. 2. For purposes of description, the orientation of various features of the device will be described with respect to a longitudinal axis X-X, a transverse axis Y-Y, and a vertical axis Z-Z. The longitudinal axis X-X, which extends into the page in FIG. 1, is oriented generally parallel to the major direction of fluid flow through the device 1 (i.e., the direction of highest fluid flow velocity), which occurs between an inlet 3 and an outlet 5 of the microfluidic chamber. The vertical axis Z-Z extends between a top surface 7 and a bottom surface 9 of the microfluidic device 1 and is oriented perpendicularly to the longitudinal axis X-X. The transverse axis Y-Y is oriented perpendicularly to both the longitudinal axis X-X and the vertical axis Z-Z. As used herein, the directions up and down, top and bottom, upper and lower are with respect to the vertical axis.

As shown in FIGS. 1 and 2, the device 1 includes a trapping component 11 that at least partially defines an upper boundary of a fluidic chamber 13. A cell trap array 15 is patterned on the underside of the trapping component 11. Individual cell traps 15a, 15b of the cell trap array 15 extend downward from the inner surface 17 of the trapping component 11 and into the fluidic chamber 13. The device 1 further includes a channeling component 19 that is positioned beneath and affixed to the trapping component 11. The channeling component 19 at least partially defines a lower boundary/lower surface 21 of the fluidic chamber 13. The channeling component 19 includes a nanochannel array 23. The nanochannel array 23 is in fluid communication with the fluidic chamber 13 and extends downward therefrom such that a given nanochannel extends in a direction generally parallel to the vertical axis. In the embodiment described herein, the trapping component 11 and the channeling component 19 are positioned such that a single nanochannel 23a of the nanochannel array 23 is positioned in vertical alignment with a single cell trap 15a of the cell trap array 15. However, it is also possible that multiple nanochannels may be positioned in closer proximity and vertically aligned beneath a single cell trap.

The device 1 further includes an upper electrode layer 25 and a lower electrode layer 27, each in fluid communication with fluidic chamber 13. The upper and lower electrode layers 25, 27 are configured and oriented to generate an electric field within the fluidic chamber 13. In the embodiment shown in FIGS. 1 and 2, the upper electrode layer 25 is positioned on a lower, inner surface 17 of the trapping component 11 and in fluid communication with the fluidic chamber 13. A reservoir 29 is positioned beneath the channeling component 19, and the lower electrode layer 27 at least partially defines the lower boundary of the reservoir 29. The upper boundary of the reservoir 29 is at least partially defined by the channeling component 19, such that the reservoir is in fluid communication with the fluidic chamber 13 via the nanochannel array 23. During use, the reservoir 29 may be filled with a transfection reagent solution 31, which travels through the nanochannel array 23 when an electric field is applied to the fluidic chamber 13 via upper and lower electrode layers 25, 27. The side boundaries of the reservoir 29 can be at least partially defined by a spacing material 33. In some embodiments, the spacing material 33 is formed of polydimethylsiloxane (PDMS).

The nanochannel array 23 can be fabricated using microfabrication techniques that will be described in greater detail below. The nanochannel height should be great enough to accelerate the molecules in the high electric field zone (i.e., inside the nanochannel), but also small enough to enable long DNA molecules to squeeze through in a brief electric pulse. In some embodiments, the nanochannels of the nanochannel array 23 can have a height in the vertical direction that can range from about 1 micrometer to about 20 micrometers (including about 1 micrometer, about 2.5 micrometers, about 5 micrometers about 7.5 micrometers, about 10 micrometers, about 12.5 micrometers, about 15 micrometers, about 17.5 micrometers and about 20 micrometers). The nanochannels can have a diameter of from about 1 nanometer to about 999 nanometers (including about 1 nanometer, about 50 nanometers, about 100 nanometers, about 150 nanometers, about 200 nanometers, about 250 nanometers, about 300 nanometers, about 350 nanometers, about 400 nanometers, about 450 nanometers, about 500 nanometers, about 550 nanometers, about 600 nanometers, about 650 nanometers, about 700 nanometers, about 750 nanometers, about 800 nanometers, about 850 nanometers, about 900 nanometers, about 950 nanometers, and about 999 nanometers. In some embodiments, the height of the nanochannels, the diameter of the nanochannels, or both may vary across the nanochannel array.

Figure 3:
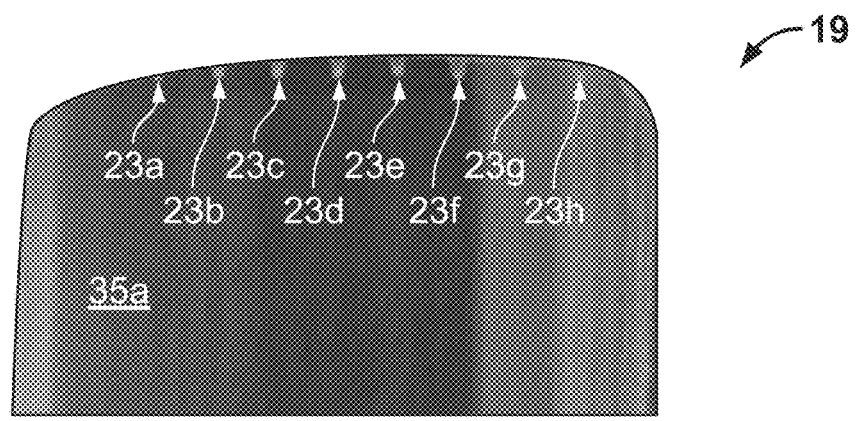
FIG. 3 is a cross sectional SEM photograph of a plurality of nanochannels meeting a microchannel within an embodiment of the channeling component of a high throughput electroporation device.

In some embodiments, the nanochannels of the nanochannel array 23 extend entirely through the height of the channeling component 19. In other embodiments, the channeling component 19 can further include microchannels 35 extending upward from a lower surface 37 of the channeling component 19 to meet the nanochannels. The microchannels 35 can be in fluid communication with the reservoir 29 beneath the channeling component 19 and in fluid communication with one or more nanochannels of the nanochannel array 23. The microchannels 35 therefore create a fluid path for the flow of transfection reagent solution 31 during electroporation. FIG. 3 shows a cross sectional photograph of the channeling component 19, wherein multiple nanochannels 23a-23h are fluidically connected with a single microchannel 35a.

Figure 4:
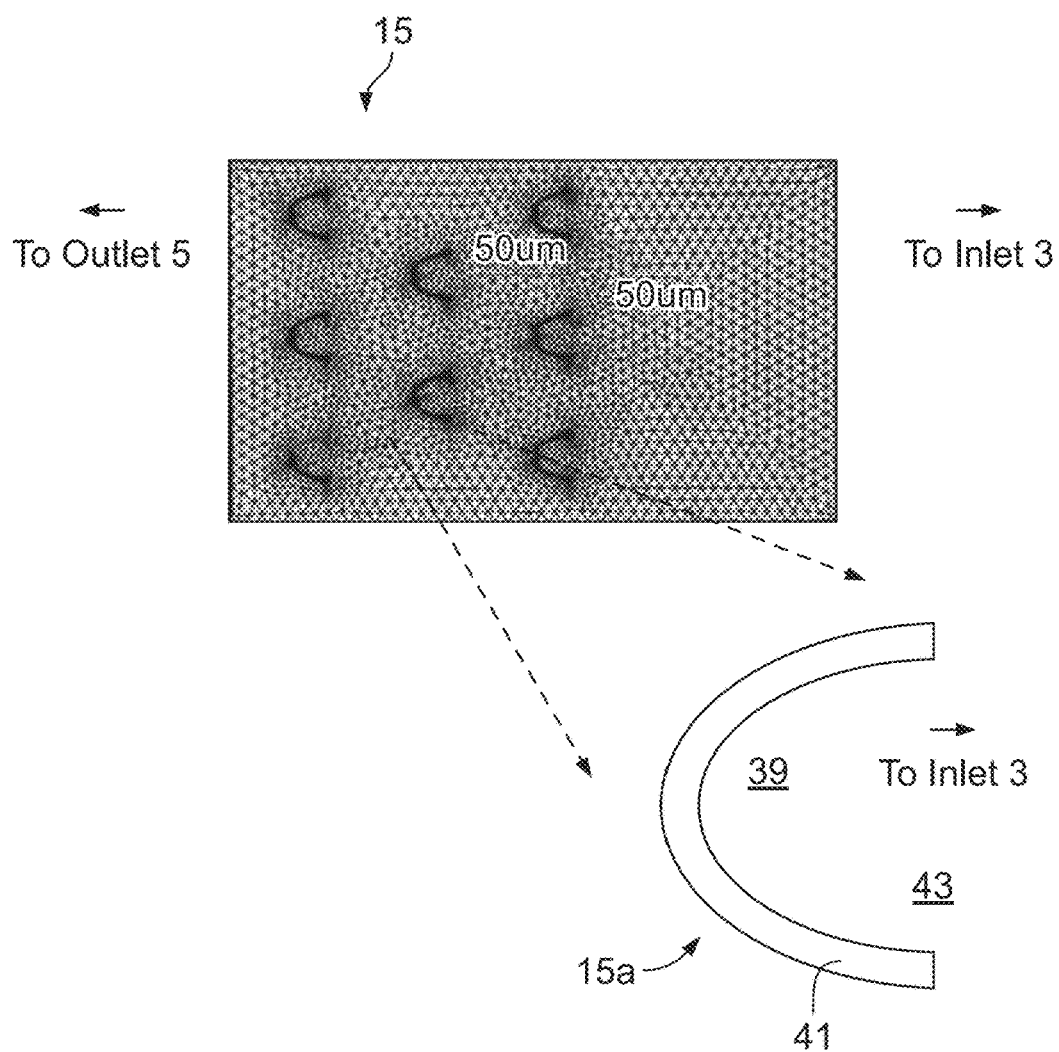
FIG. 4 shows a portion of a cell trap array (top) with a single cell trap enlarged (bottom) for ease of visualization of certain features.

The trapping component 11 is designed to immobilize cells in both the longitudinal and vertical directions, removing them from the fluid flow while also pushing them down against a nanochannel of the nanochannel array, creating close contact for electroporation. As shown in FIG. 4, each cell trap 15a of the cell trap array 15 comprises a cupping region 39 partially defined by walls 41 of the cell trap 15a. The cupping region 39 includes an entry portion 43 oriented toward an inlet 3 of the fluidic chamber 13. In the embodiment shown, the walls 41 of the cell trap 15a partially curve around the cupping region 39 in a U-shape. However, the walls 41 could instead be straight, taking a partially triangular (V-shape) or a partially rectangular shape whilst still forming a cupping portion 39 and an entry portion 43 with the capacity for trapping cells. The fluidic chamber 13 is oriented along the longitudinal axis X-X such that the longitudinal axis X-X generally extends between the inlet 3 and outlet 5, as shown in FIGS. 1 and 2. The cupping region 39 of a given cell trap 15a faces the inlet 3 side of the fluidic chamber 13 so as to capture cells during fluid flow.

Figure 5:
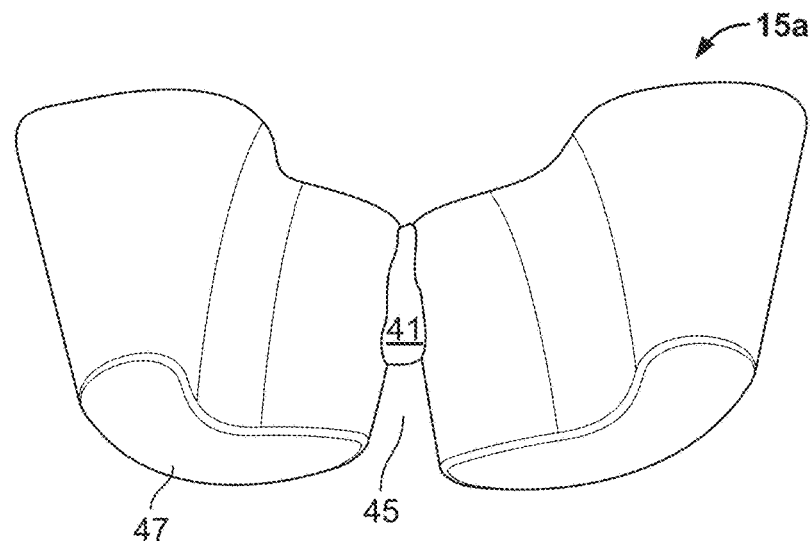
FIG. 5 is an SEM photograph of an embodiment of a cell trap.
Figures 9A, 9B, 9C:
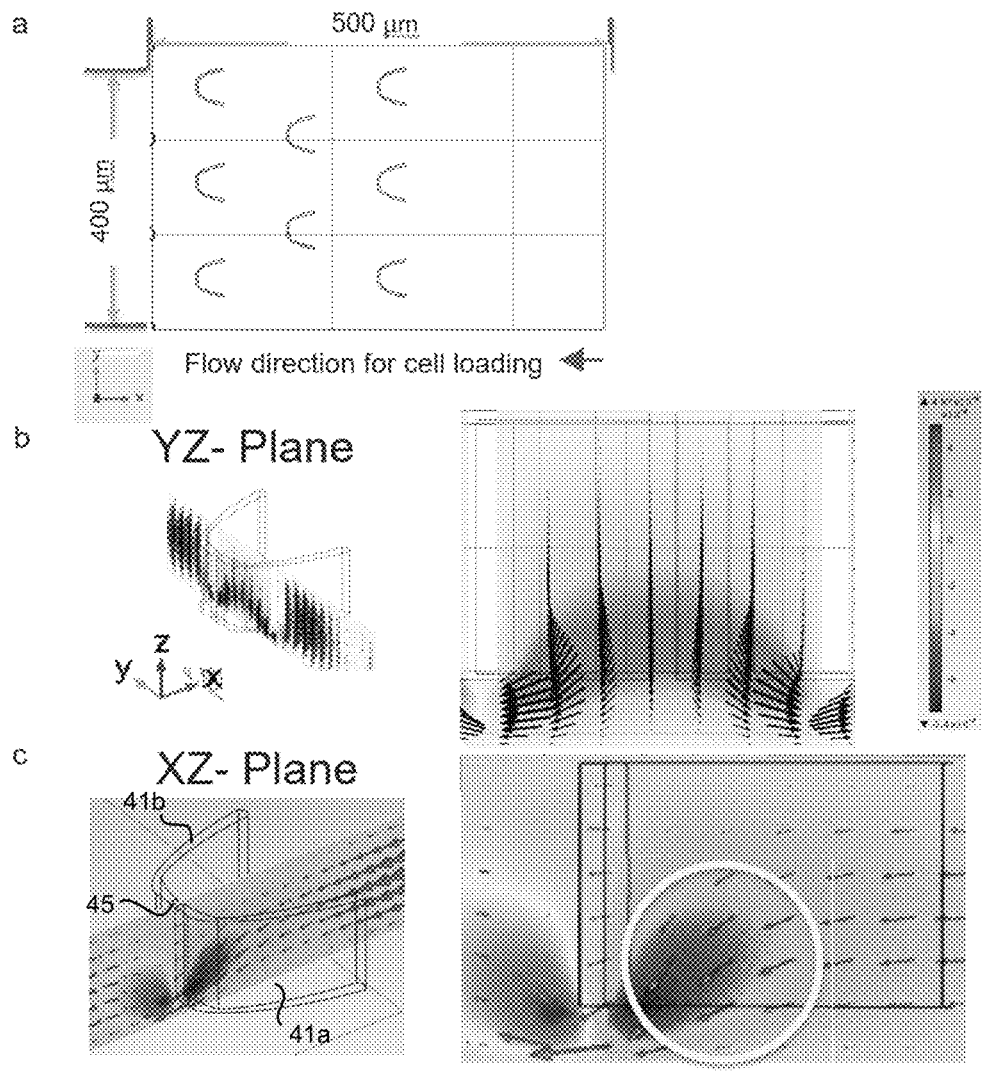
FIGS. 9A-9C show modeling of the microfluidic cell trap (no herringbone pattern) and FEM simulation result.

A cell trap 15a may have a single wall 41 creating a cupping region 39, or it may have two half-walls 41a, 41b creating a cupping region 39 and leaving a small fluid exit gap 45 between them, as shown in FIG. 9C. The fluid exit gap 45 is smaller than a captured cell, such that a cell caught in the cupping region 39 cannot escape through the fluid exit gap 45. Some embodiments, such as the one shown in FIG. 5, include a single wall 41 defining a cupping region 39 and also including a partial fluid exit gap 45 extending upward from the lower edges 47 of the wall. The partial fluid exit gap 45 extends only partially up the wall 41 so as to allow fluid flow through an empty cell trap 15a while also maintaining capture of a trapped cell. This partial fluid exit gap also helps to generate downward pushing force on a trapped cell and facilitate close contact of trapped cell with nanochannel during electroporation. In some embodiments, such as the one shown in FIG. 4, the cell traps of the cell trap array 15 are positioned in staggered rows. However, the positioning of the cell traps with respect to each other can vary. The dimensions of the cell traps can be tailored to suit the particular type of cell they are designed to capture. In an Example described below, a cell trap is designed to capture a mouse embryonic fibroblast, and is sized accordingly at 15 microns wide, 12 microns long and 15 microns in height. However, the dimensions of the cell traps can vary and are not meant to limit the invention.

Figure 6:
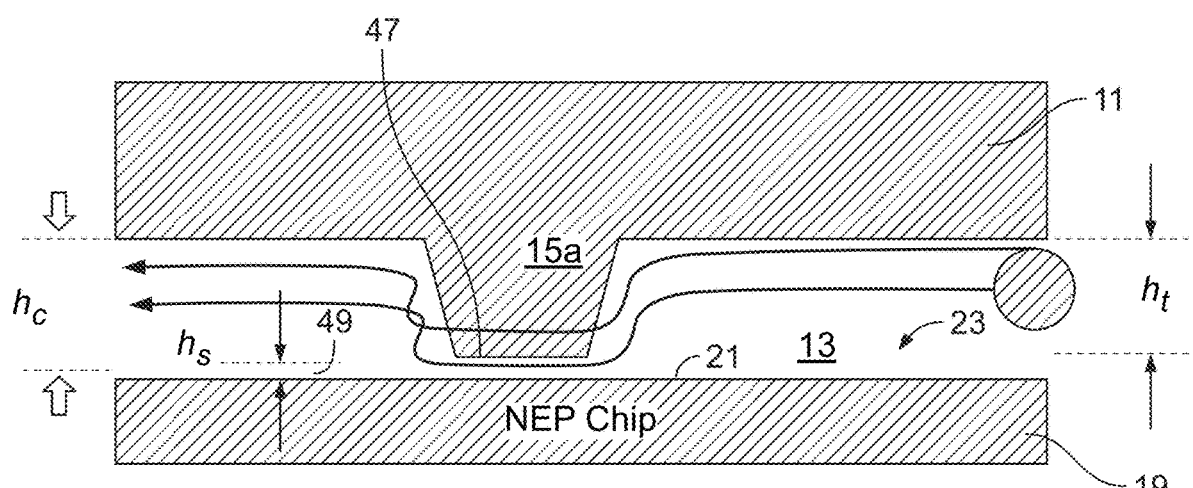
FIG. 6 is a cross-sectional schematic of an embodiment of a trapping component, a fluidic chamber, and a channeling component of a high throughput electroporation device.
Figure 7:
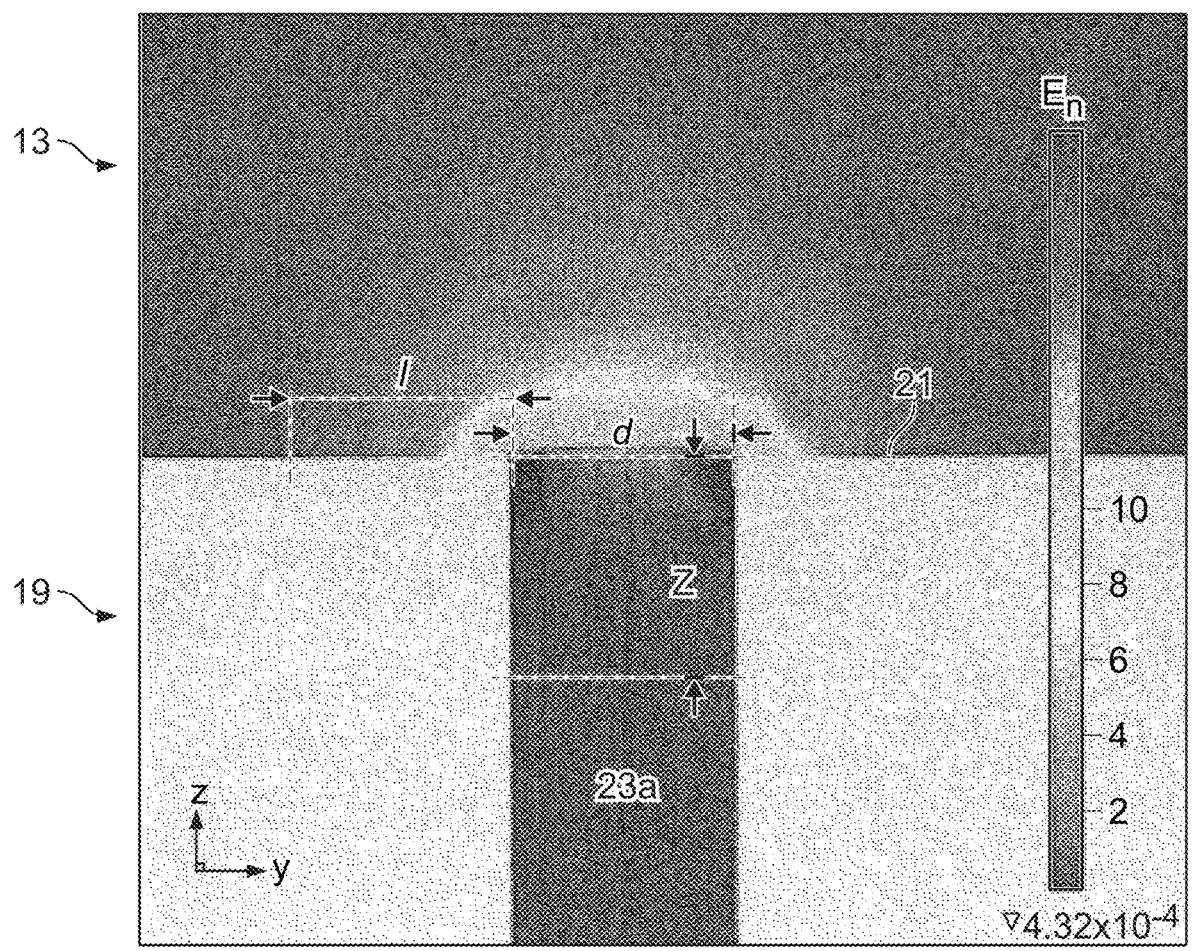
FIG. 7 is a cross-sectional schematic of an individual nanochannel meeting the fluidic chamber of a high throughput electroporation device.
Figures 8A, 8B, 8C, 8D:
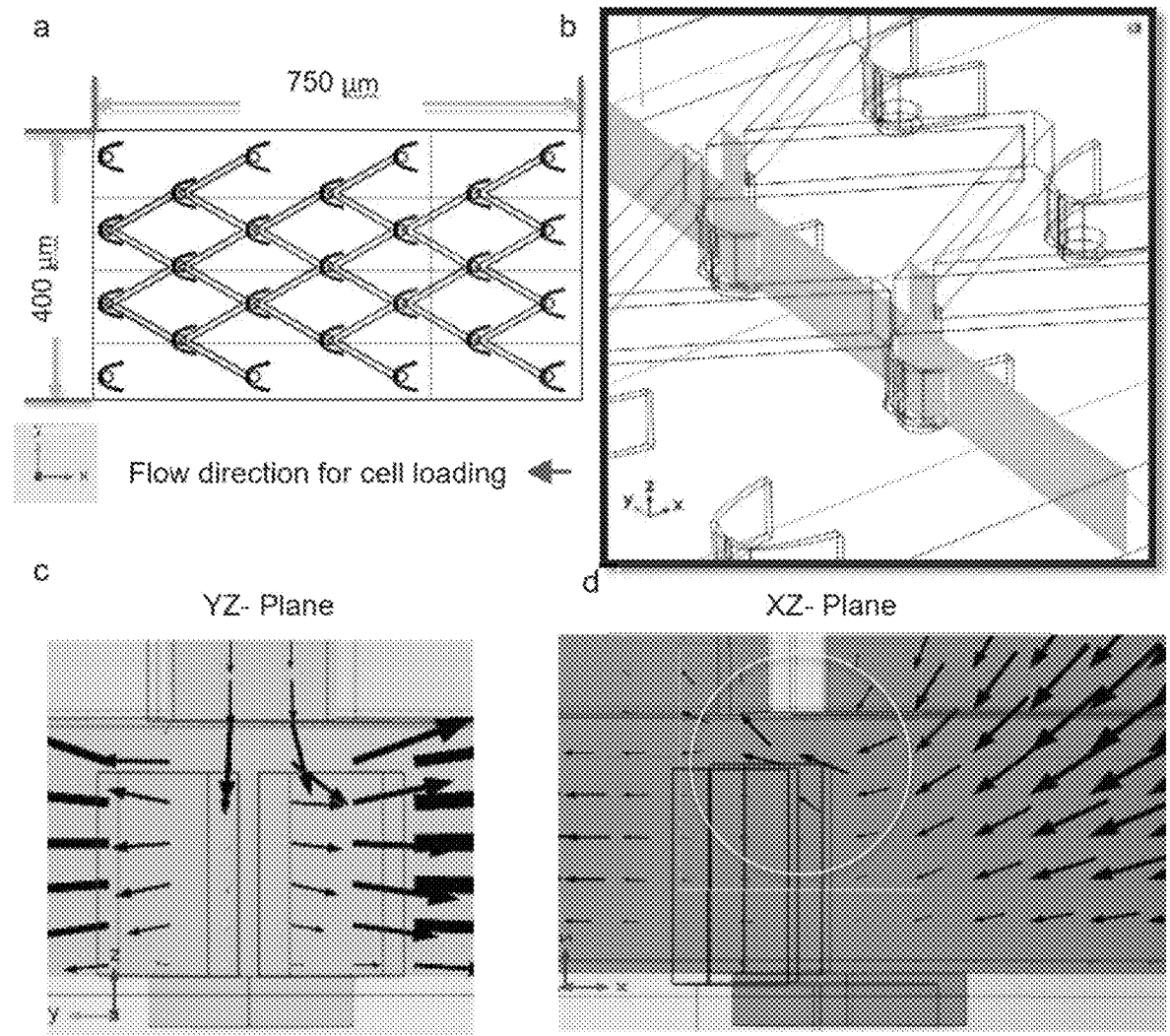
FIGS. 8A-8D show modeling of a "bottom" standing microfluidic cell trap (with a herringbone pattern) and FEM simulation results.

The cupping region 39 is positioned above at least one nanochannel of the nanochannel array 23. Furthermore, as shown in FIG. 6, the trapping component 11 is designed such that the height $h_t$ of a cell trap is slightly less than the height $h_c$ of the fluidic chamber 13 ($h_c$ as measured between lower boundary 21 of the fluidic chamber and lower inner surface 17 of trapping component 11), thereby creating a space 49 between the lower edge 47 of each cell trap 15a and the channeling component 19. The height $h_s$ of the space 49 is the difference between $h_c$ and $h_t$. The space 49 beneath the cell trap lower edge 47 enables fluid flow underneath the cell trap 15a when it is empty. The height of the space 49 is less than that of a cell so that captured cells cannot squeeze underneath the lower edge 47 of the cell trap wall. This cell trap construction contributes to the slowing of the flow velocity within the cupping region 39 and the downward fluidic force that traps the cell against the channeling component 19 to ensure contact with a nanochannel. The fluidic dynamics will be discussed in greater detail in the Examples, below.

In some embodiments, the trapping component 11 can be fabricated using soft lithography techniques. A silicon master wafer is patterned via contact lithography with the inverse microscale cell trap array design. The silicon wafer is then used as a master mold for casting PDMS to create the trapping component 11.

In some embodiments, the nanochannel array 23 on the upper side of the channeling component 19 is formed by a combination of projection lithography to pattern nanopores on a silicon wafer, followed by a deep RIE (Bosch Process) etching process. Alternating etch and sidewall passivation creates high aspect ratio (>15:1, in some embodiments >20:1) nanochannels. In other embodiments, the nanochannel array 23 can be formed of polymer or a thin and flexible biocompatible film using other fabrication techniques. Microchannels 35 can be formed on the lower side of the channeling component 19 using contact lithography techniques. Surface modification (such as, for example, PEG surface grafting) can also be performed to prevent cells from adhering to the channeling component 19. The trapping component 11 and channeling component 19 can be affixed to each other using oxygen plasma bonding techniques. In some embodiments, a gold-coated glass slide acts as the lower electrode, and a partial layer of spacing material 33 distances the lower electrode 27 from the channeling component 19. The inner boundaries of the spacing material 33 define a reservoir 29, as described above.

Example methods of high throughput cell electroporation will now be described with respect to the embodiments shown in FIGS. 1-7 and described above. However, it is to be understood that the methods disclosed herein can be used with other structural embodiments of the high throughput cell electroporation device without deviating from the inventive concepts.

To initiate the electroporation process, a cell suspension is flowed in a forward direction through inlet 3 of fluidic chamber 13. In some embodiments, the flow velocity at the inlet 3 is from about 70 to about 130 microns per second, including about 70 microns per second, about 80 microns per second, about 90 microns per second, about 100 microns per second, about 110 microns per second, about 120 microns per second, and about 130 microns per second. The density of the cell suspension may vary depending upon the cell type, but is typically between from about 3 to about 15 million cells/mL, including about 3 million cells/mL, about 4 million cells/mL, about 5 million cells/mL, about 6 million cells/mL, about 7 million cells/mL, v 8 million cells/mL, about 9 million cells/mL, about 10 million cells/mL, about 11 million cells/mL, about 12 million cells/mL, about 13 million cells/mL, about 14 million cells/mL, and about 15 million cells/mL.

Some of the cells of the cell suspension are trapped by the cupping regions 39 of the cell trap array 15 in the fluidic chamber 13, and the fluidic patterns created around the individual cell traps (due to the continued forward flow of the fluid, from inlet to outlet) position at least a portion of the trapped cells into secure contact with the nanochannels 23 that extend downward from the lower boundary 21 of the fluidic chamber 13. The secure contact is not permanent, but is instead a product of the fluid dynamics of the forward flow and the structure of the cell trap 15a. In some embodiments, the flow within at least a portion of the cupping region 39 of the cell trap 15a is completely stopped or slowed significantly, thereby creating a "safe harbor" for the cell wherein fluid shear is eliminated or completely diminished, advantageously increasing cell survival rates. In some embodiments, the flow within at least a portion of the cupping region 39 is no more than about 20% of the inlet flow velocity (including no more than about 1%, no more than about 5%, no more than about 10%, no more than about 15% and no more than about 20% of the inlet flow velocity). Due to the unique design, the at least 75% of the cells of the initial cell suspension are trapped by device 1 during flow (including about at least 75%, about at least 80%, about at least 85%, about at least 90%, and about at least 95% of the initial cell suspension).

While the trapped cells are securely contacting the nanochannels 23, they are subjected to electroporation via an electric field created between the upper and lower electrodes 25, 27. In some embodiments, the voltage applied between the upper and lower electrodes 25, 27 for electroporation is from about −50V to about −500V (including about −50V, about −100V, about −150V, about −200V, about −250V, about −300V, about −350V, about −400V, about −450V, and about −500V). The voltage can be applied as pulses that range in duration from about 1 millisecond to about 100 milliseconds, including about 1 millisecond, about 10 milliseconds, about 20 milliseconds, about 30 milliseconds, about 40 milliseconds, about 50 milliseconds, about 60 milliseconds, about 70 milliseconds, about 80 milliseconds, about 90 milliseconds, and about 100 milliseconds. Anywhere from 1 to 20 pulses can be delivered during an electroporation protocol (including 1 pulse, 2 pulses, 3 pulses, 4 pulses, 5 pulses, 6 pulses, 7 pulses, 8 pulses, 9 pulses, 10 pulses, 11 pulses, 12 pulses, 13 pulses, 14 pulses, 15 pulses, 16 pulses, 17 pulses, 18 pulses, 19 pulses, and 20 pulses). The rate of cell electroporation is high by conventional standards. For time periods greater than 10 minutes, the rate of cell electroporation is greater than about 1,000 cells per minute per square centimeter of microfluidic chamber, including greater than about 1000 cells per minute per square centimeter, greater than about 1250 cells per minute per square centimeter, greater than about 1500 cells per minute per square centimeter, and greater than about 2000 cells per minute per square centimeter.

The electric field extends through and immediately adjacent to each individual nanochannel 23a, such that cells in secure contact with the nanochannel are subjected to electroporation. Interestingly, the electric field strength drops sharply as the lateral distance from a nanochannel increases. This helps to ensure that only trapped cells are electroporated, thereby increasing the precision of transfection. For example, this concept can be described with reference to FIG. 7. A nanochannel has a particular nanochannel diameter d at the lower boundary 21 of the microfluidic chamber 13. A nanochannel electric field strength $E_n$ can be measured at a depth z beneath the lower boundary 21 of the microfluidic chamber 13 that is equivalent to the nanochannel diameter (z=d). Within the microfluidic chamber, at a lateral distance l away from a side of the nanochannel that is equivalent to the nanochannel diameter (l=d=z), the strength of the electric field is less than about 20% the strength of the electric field within the nanochannel (including less than about 15%, less than about 10%, less than about 5%, and less than about 1%).

In some embodiments, the cells are transfected while trapped and during the electroporation. The transfection reagent solution 31 housed in reservoir 29 may include genetic material, drugs, proteins, molecular probes, nanoparticles, and/or sensors for incorporating into the cell. In some embodiments the cells are transfected with genetic material during electroporation, including strands of genetic material of up to 100,000 base pairs. For bulk electroporation transfection, large molecules such as these can only partially attach to the cell membrane and later may be endocytosed. Because of this, transfection efficiency for larger molecules using bulk electroporation is relatively low. By contrast, the transfection described herein is highly efficient, even for larger molecules. Cell survival is also quite high by conventional standards (90% or greater after full transfection). The devices and methods disclosed herein also provide excellent dosage control (that is, the amount of cargo delivered into the cells can be precisely controlled by setting the electric pulse parameters). Other transfection methods (viral transfection, nanoparticles, or bulk electroporation, for example) often involve stochastic processes, such as diffusion and endocytosis, during cell transfection, leading to high variability in dosage of transfection.

After the electroporation, the cells are released from the cell trap array 15 and collected. For release, the forward flow of the fluid can be slowed or stopped. In some embodiments, the fluid flow is reversed (from outlet to inlet) to facilitate collection of the cells. Fluid flow can be automated, for example, by using one or more digital flow controllers to control bidirectional valves at the inlet and outlet of the fluidic chamber. For example, a digital flow controller can automate control of buffer washing, cell loading, electroporation, and cell collection.

EXAMPLES

Example 1: CFD Simulation of Flow Velocity Field in the Microfluidic Cell Trap Design The U-shaped micro-trap structure has been proven to be effective for trapping individual cells via a hydrodynamic force (Skelley et al., 2009). Herein, two microfluidic cell trap array designs (i.e. "bottom" standing on substrate or "top" hanging from ceiling, FIGS. 8A-8D and 9A-9D) were studied and compared using the FEM simulation with focus on the flow velocity field near the cell trap region. This analysis provided an insight on whether the local flow within the cell trap chamber could facilitate a close contact of the trapped cell with the nanochannel outlet.

The geometry of the cell trap array was designed according to the size of mouse embryonic fibroblast (MEF) cells, with an average diameter of ~15 the width and length of the cell trap were set to be W=L=15 μm, and the height of the cell trap was set to be H=20 μm. The cell trap array was arranged to be interleaved instead of parallel because this design could provide superior particle trapping efficiency compared to parallel array (Chang, Gallego-Perez, et al., 2016). The nanochannel array was neglected in this microfluidic modeling and simulation, as it was assumed that the nanochannel located at the center of each cell trap would not affect the outlet of flow, considering the extremely high pressure needed to drive any fluid through the nanoscale channel.

The "bottom" standing micro trap array patterned on a silicon chip substrate was analyzed first (FIGS. 8A-8D). Not surprisingly, an upwards flow velocity was observed in the micro trap region. This is because the cell trap essentially functions as a "wall" near which the fluid cannot flow through but can only change the direction to go upwards and pass through the gap between the cell trap and the microfluidic channel ceiling. Although the flow velocity in the x-y plane will guide the individual cells towards the cell traps, the upwards flow velocity within the chamber of the cell trap will keep pushing the cell up away from the nanochannel.

To suppress the upward flow caused by the cell trap on the substrate and to ensure a tight contact between captured cells and nanochannels, a herringbone structure aligned with the cell trap array is added to the modelling of a flow area of 750 μm×400 μm (FIGS. 8A-8B) The herringbone structure is designed to extend downward from the ceiling of the PDMS microfluidic device. Such microfluidic herringbone structure designed on the ceiling of microfluidic devices has been found to be able to generate vortices in the microscale, thus increasing the cell capture efficiency (Stott et al., 2010). The FEM simulation result (FIGS. 8C-8D) shows that this herringbone pattern with the optimized geometry can indeed generate a downward flow velocity in the proximity of the micro-trap and thus can help guide the individual cells onto the micro-traps. However, within the micro trap chamber, the downward z component of the flow velocity is very small and there still exists an upward flow near the gap between the top of the micro trap and the ceiling (FIG. 8D), which may lift the captured cell away from the nanochannel outlet on the bottom substrate. Thus, even though this "bottom" standing design is good for cell capture, its NEP transfection could be compromised due to the loose contact between the cell and the nanochannel.

In comparison, the FEM simulation shows that no additional herringbone structure is needed to secure cell capture within the cell trap if the cell trap array is to be built on the ceiling of the PDMS microfluidic device (FIGS. 9A-9C). The "top" hanging U-shaped cell trap structure can not only capture a cell with a proper size same as in the previous "bottom" standing design, but also function as a "wall" that re-orients the flow downwards to pass through the gap between the silicon NEP chip substrate and the PDMS cell trap (FIG. 9C-9D). The FEM simulation results show that in the gap between the micro trap and the bottom substrate, the flow velocity magnitude is ~1 μmm/s with a z component ~0.5 μm/s, which can generate a piconewton-level "pushing" force according to Stokes' law. This hydrodynamic drag force exerted on the captured cells will secure their tight contact with their corresponding nanochannels underneath and thus lead to good NEP transfection.

Figure 10:
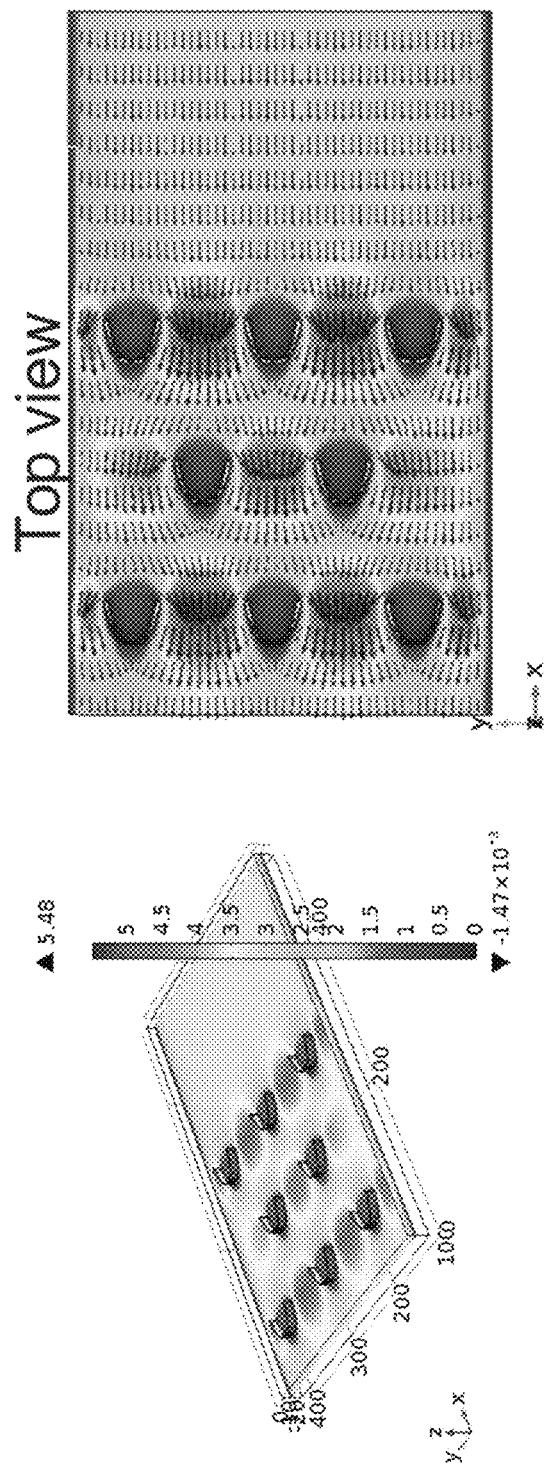
FIG. 10 shows the "safe harbor" regions within the cell traps. Simulation results of the flow velocity field (directional arrows) in the x-y plane and the velocity magnitude (indicated by color legend, unit: μm/s). Blue color regions within the cell trap had a negligible flow velocity, protecting captured cells from excessive drag force and shear stress.

As shown in FIG. 10, another benefit of hydrodynamic weir-like microstructures for cell trap is that the cell capture chamber may serve as a "safe harbor", within which the flow velocity is much lower (<0.5 μm/s) compared to that in the region outside (>5 μm/s). This "safe harbor" could protect the captured cells from excessive drag force and shear stress even if a large flow rate is applied for the rapid cell trapping.

While both microfluidic cell trap designs given in FIGS. 8A-8D and 9A-9C can position the cells in the traps, the "top" hanging cell trap design extruded from the PDMS ceiling is more advantageous because of its ability to exert an additional "pushing" force on the cells towards the nanochannel outlets during flow and its simplicity for fabrication and easy for device assembly. As such, the design of FIGS. 9A-9C was chosen for further investigation.

Figures 11A, 11B, 11C, 11D, 11E, 11F, 11G:
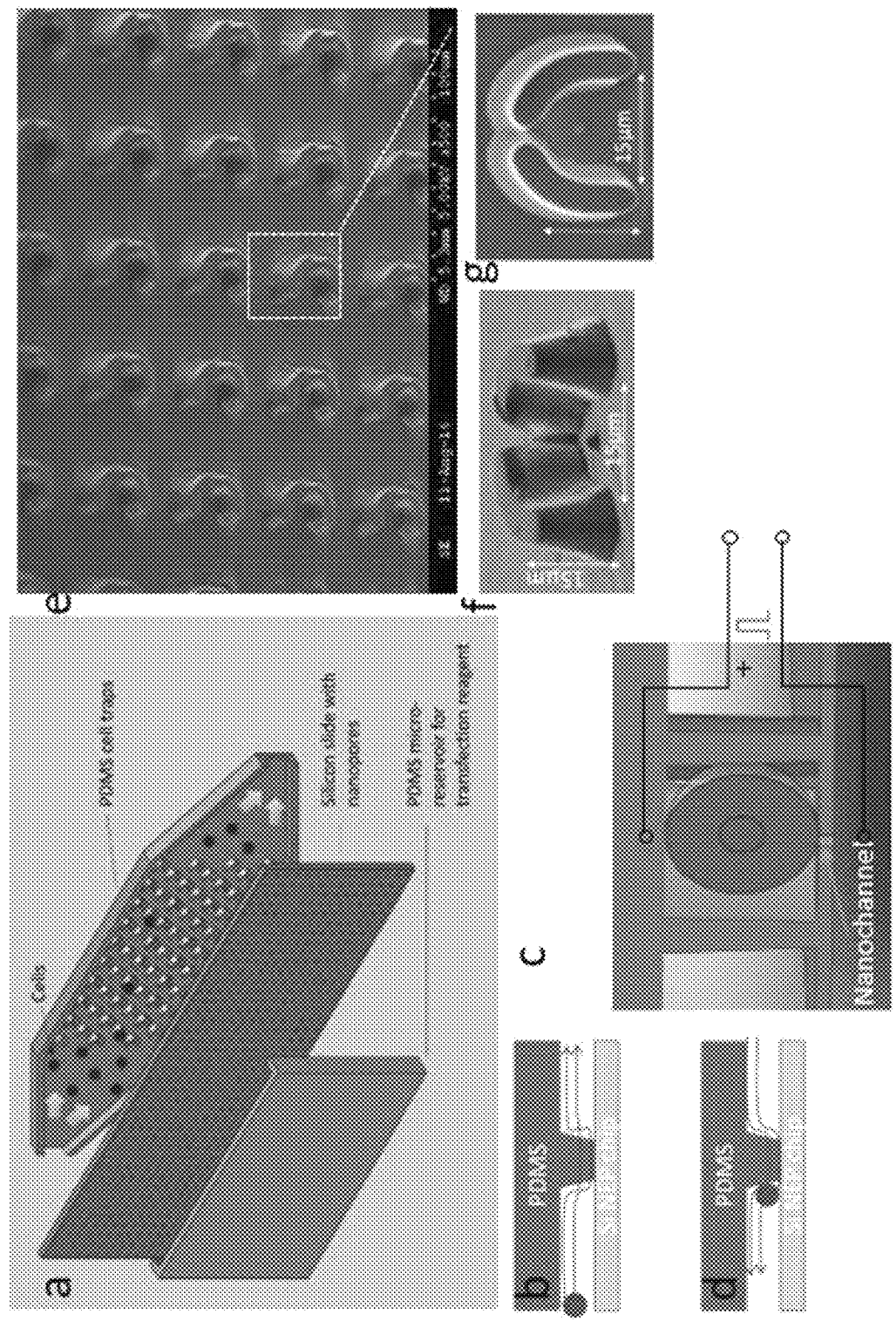
FIGS. 11A-11G show a device design for a microfluidic cell trapping and high-throughput 3D NEP transfection.

Example 2: Microfluidic-Cell-Trapping-Assisted 3D High-Throughput NEP Platform Design As shown in FIG. 11a, this microfluidic-cell-trapping-assisted 3D NEP device is comprised of three main layers of solid materials from top to bottom: Layer 1—a wide PDMS microfluidic channel with a patterned micro-trap array for capture of up to 20,000 cells, Layer 2—a silicon substrate with a dense nanochannel array, and Layer 3—a gold-coated glass slide as the bottom electrode.

Cell suspension in the buffer solution is added from the microfluidic channel inlet on the left and flows through the microfluidic channel driven by the pressure generated by a syringe pump. Cells are captured by the weir-like micro traps, ready for nano-electroporation (FIG. 11b). The cells that are not trapped will flow through and can be collected at the outlet and re-used in the next cell trapping cycle. Experimentally, an upright microscope (Leica Microsystems DM12500 MH) was used for real-time monitor of the cell capture process. When the cell trap array was nearly saturated (>90%), the NEP-based transfection was performed while the flow continued in order to keep holding the trapped cells against nanopores on the silicon substrate via a hydrodynamic force. Transfection reagents from the micro-reservoir between Layer 2 and Layer 3 were electrophoretically injected into nanoporated individual trapped cells by applying a focused electric field through the nanochannels (FIG. 11c). Square wave electric voltage pulses (voltage 220 V, pulse duration 10 ms, 1-5 pulses) for nano-electroporation were generated from a power supply (Gene Pulser, Bio-Rad). An inverted microscope (Nikon Eclipse Ti) was used to check the fluorescence of the transfected cells post-NEP. After NEP, the flow direction was simply reversed to release and collect the transfected cells from cell traps at the inlet (FIG. 11d).

Example 3: Fabrication of the Microfluidic Cell Trap Array

According to previous FEM simulation results, the cell trap array was located on the microfluidic channel ceiling. Fabrication of the PDMS microfluidic channel with the cell trap array was based on soft lithography. The micro-fabricated cell trap array structure is shown in FIG. 11e and a detailed geometry of single cell trap is: 15 μm wide, 12 μm long and 15 μm in height, which is confirmed by zoom-in SEM micrographs showing in FIG. 11f-g. A gap in the middle of the trap is designed to let the fluid pass through.

Figure 12:
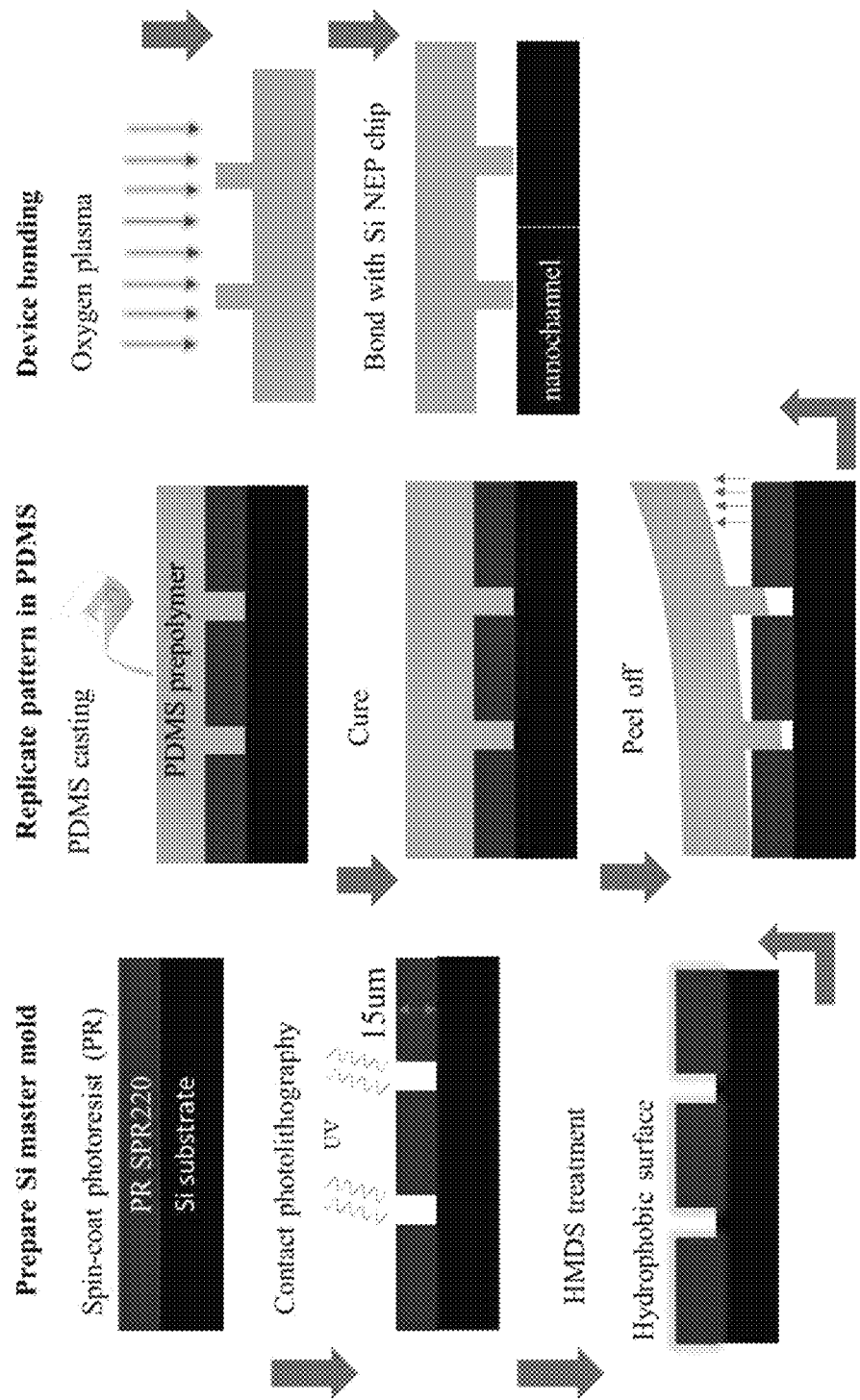
FIG. 12 shows a representation of a soft-lithography-based fabrication protocol for a PDMS microfluidic channel with a cell trap array.

The fabrication procedure is illustrated in FIG. 12. Briefly, the Si master wafer was patterned with the microscale cell trap array via contact photolithography (EV Group 620 Contact Aligner). In the replica-molding process, a 10:1 mixture of PDMS (Sylgard® 184, Dow Corning) was spin-coated on the pre-defined Si master wafer at 300-500 rpm for 1 min, and then vacuumed for 30 min in a desiccator. After the mixed PDMS polymer solution cured at room temperature for at least 48 h, a demolding step was carried out by carefully peeling off the cured PDMS film from the Si substrate.

Example 4: Fabrication and Characterization of Nanochannel Array Device

Wafer-Scale Fabrication of High-Throughput Silicon NEP Chip

Figures 13A, 13B:
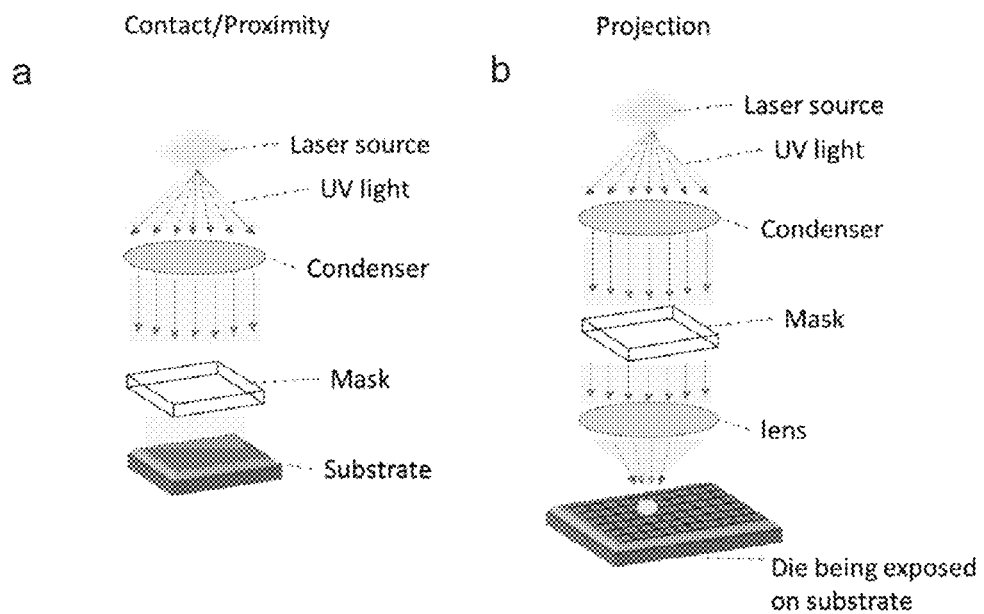
FIGS. 13A-13B show a schematic of different types of optical lithography (FIG. 13A) contact/proximity photolithography, in which a uniform light is exposed on the entire sample, (FIG. 13B) projection photolithography, in which the mask (or reticle) is projected on a portion of the sample, known as "die". The complete pattern is created by sequential exposure for multiple times.
Figures 14A, 14B:
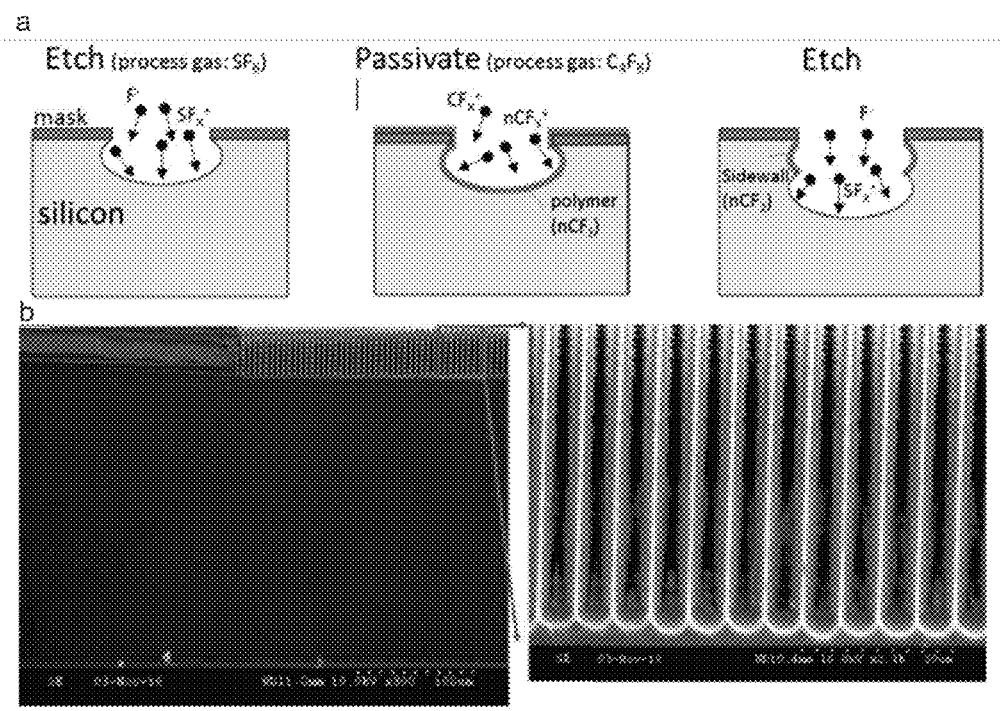
FIGS. 14A-14B show the high-aspect ratio (>20:1) micro-/nano-structures achieved by Bosch Process etching.

The nanochannel array on a silicon substrate as a 3D NEP platform was fabricated in a Class 100 cleanroom, after a series of optical lithography (including contact/proximity photolithography and projection photolithography, as illustrated in FIG. 13) and Bosch-Process-based deep reactive ion etching (DRIE) steps (as shown in FIG. 14) on both sides of <100> double-polished 4-inch silicon wafer (purchased from University Wafer Inc., 850 Summer St., Suite #207, Boston, Mass. 02127, USA, Item #2345). The detailed fabrication protocol is discussed below, in the manner of time order.

Patterning Nanochannel Array by Projection Photolithography

To pattern the nanopores with a diameter of 500 nm, projection lithography was used to shrink (5×) and print the nanopore array from the pre-designed micropore pattern (2.5 μm in diameter) on a photomask. The schematics showing photolithography principles are given in FIGS. 13a-13b. Basically, contact/proximity lithography (FIG. 13a) imprinted 1:1 the exact size of the pattern on the photomask into the sample, and projection lithography (FIG. 13b) reduced the pattern on the photomask (or reticle) by adding an objective lens below and projecting the pattern on a small portion of the sample known as "die". Multiple exposure was often needed in projection lithography to cover the entire wafer with an array of dies. Projection lithography for the nanopore pattern was performed in the tool GCA 6100C Stepper (i-line) (STP 01, Nanotech West Lab) under optimized conditions: an exposure time of 15 sec (3 times of the recommended value to ensure full open of the nano-pore feature with a 2:1 height to diameter aspect ratio), and a focus offset 0. Post-bake was skipped, otherwise AZ5214 would yield an opposite polarity of pattern as negative PR. Lastly, the wafer was developed in MF-319 for 1 min for a good nanochannel array pattern on PR.

Etching the Nanochannel Array by Bosch Process

Herein, a deep silicon structure etching method, deep RIE (DRIE) "Bosch Process", was utilized to etch a high-aspect ratio (>20:1) nanochannel array (10 μm nanochannel depth). An alternating sequence of the etch process (SF6 gas) and the sidewall passivation step (C4F8) enabled a fast etch rate, a nearly 90° sidewall profile, and high-aspect ratio features (FIG. 14). Bosch process was carried out using the Oxford Inductively Coupled Plasma (ICP)—RIE (Dreese lab, ECE, Cleanroom) system with optimized parameters, which led to a high-quality nanochannel array.

Patterning and Etching the Microchannel Array

Figures 15A, 15B, 15C:
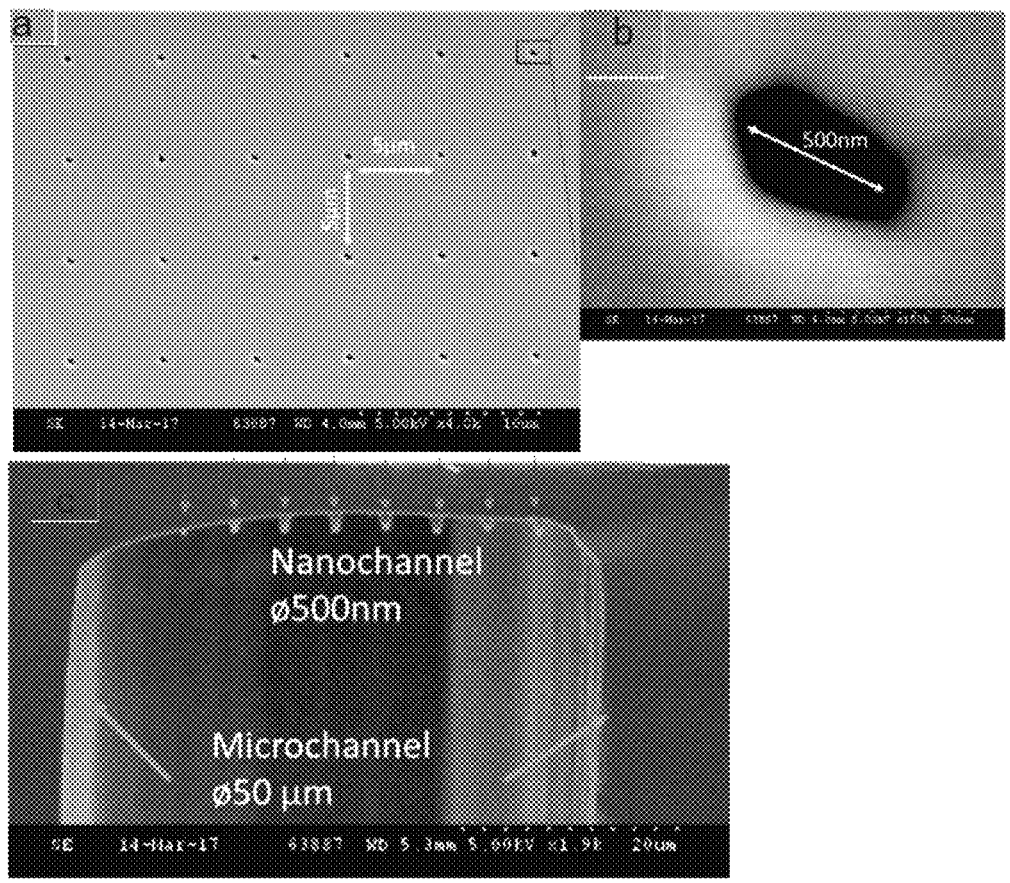
FIGS. 15A-15C show photographs of a nanochannel (φ500 nm) array fabricated by projection photolithography and deep reactive ion etching (DRIE).

A backside microchannel array is needed to produce a through channel structure which allows for NEP function. A micropore was patterned (50 μm diameter, 25 μm spacing) by contact lithography (EV Group 620 Contact Aligner, ALGN02, Nanotech West Lab). Etching of the microchannel was performed using the same DRIE tool. Repeating the cycle for 350 times would result in a 250 μm deep microchannel. Characterization was done by SEM imaging of the nanopore surface and the cross-section of the silicon NEP device, as shown in FIGS. 15A-15C.

Example 5: Cell Density for Microfluidic Cell Trapping

Figures 16A, 16B, 16C:
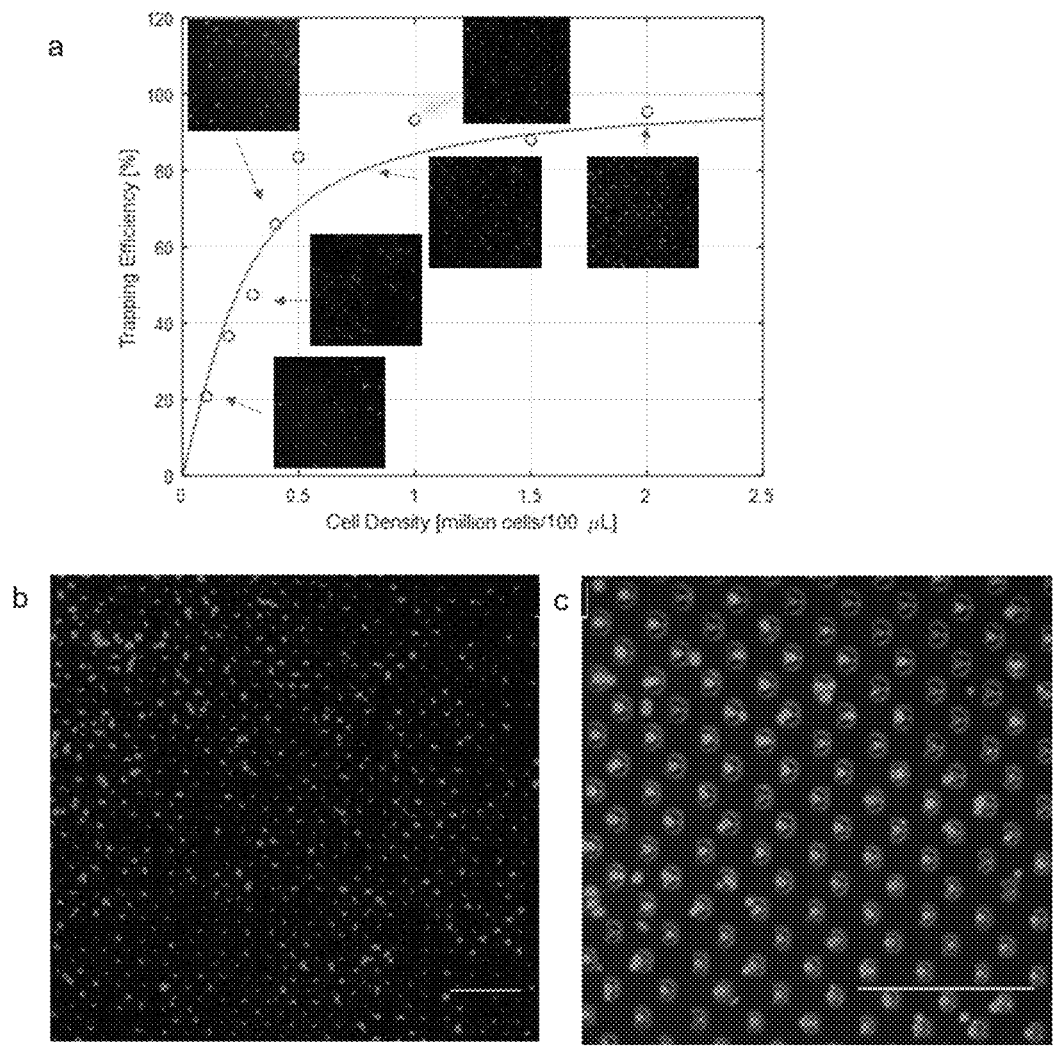
FIGS. 16A-16C show the microfluidic cell trapping results of Hoechst® stained NK92 cells (blue) using optimized conditions.

A series of cell suspension buffers with different cell densities were used to find the cell density conditions that allowed for microfluidic cell trapping at the flow rate of ~100 μm/s suggested by the literature (Skelley et al., 2009). The cell trapping duration was fixed at 2 min. After trapping, fluorescence imaging was used to check the cell trapping efficiency (the ratio of the number of occupied cell traps to the number of total cell traps). As shown in FIG. 16a, the trapping efficiency kept increasing and reached ~90% when the cell density approached 0.5~1 million cells per 100 μL. It is worthwhile to notice that there seemed to be a linear relationship between cell density and capture efficiency in the range of 0.1~0.5 million cells per 100 When the cell density was higher than 1 million cells per 100 μL, the cell capture efficiency did not improve much (~90-95%), while the probability of individual cells sticking together in the flow became larger and thus the "clogging effect" became significant with the percentage of "multiple trapping" cell traps increasing. Therefore, a microfluidic cell trapping condition was selected for the remaining experiments of the Examples: cell density 0.5~1 million per 100 µL, flow rate ~100 µm/s, and trapping duration 2 mM. A large-scale array (~1,000 cells) of captured Hoechst® stained NK92 cells (blue) is shown in FIG. 16b. A merged phase contrast and DAPI fluorescence image (FIG. 16c) showed that most of the cells (~95%) were captured by the cell trap array, as expected.

To remove the un-trapped cells (especially adherent cells with sticky membrane) within the microfluidic channel, proper surface chemical modification such as surface-grafted poly (ethylene glycol) (PEG) can be done in addition to PBS buffer washing after cell trapping.

Example 6: Cell Positioning in NEP Process

Figure 17:
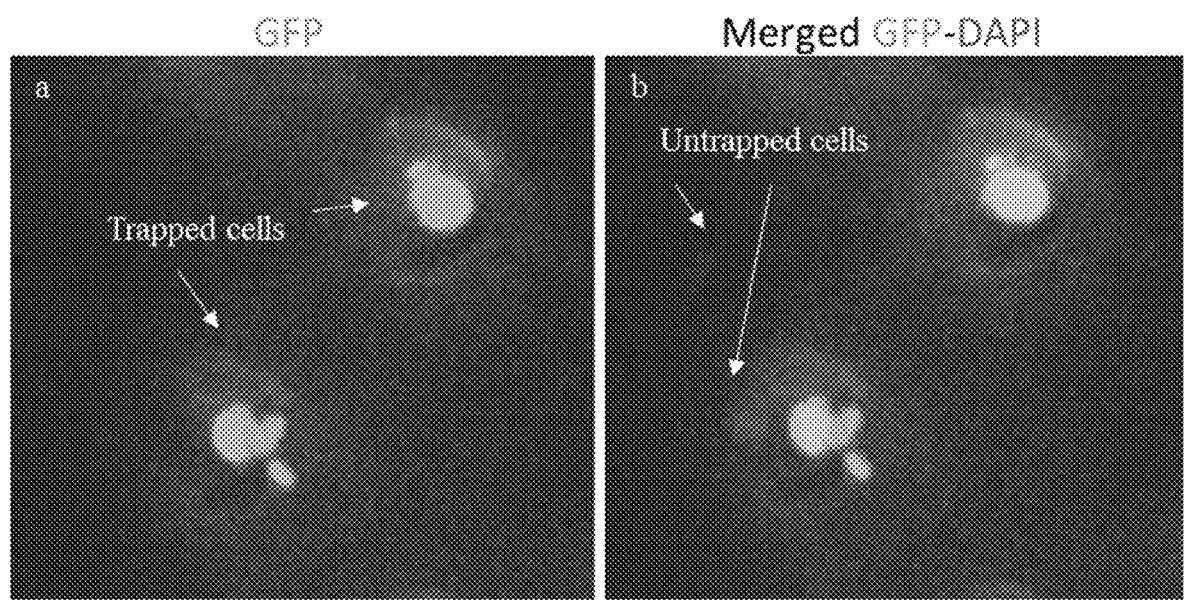
FIG. 17 shows photographs indicating that microfluidic cell trapping improved NEP-based delivery. Cells captured by the weir-like cell traps got transfected by YOYO-1-labelled plasmids showing both green and blue fluorescence (nucleus staining), while un-trapped cells only showing blue fluorescence. (a) GFP channel (b) merged GFP+DAPI channels

As mentioned earlier, close contact between the to-be-transfected single cell and the nanochannel facilitates good NEP cell transfection. As shown in FIG. 17, only the captured "trapped cells" which were pushed against the NEP silicon substrate by the hydrodynamic force generated by microfluidics were transfected as indicated by strong green fluorescence signals. On the other hand, unconstrained "Untrapped cells" showed no transfection (exhibiting only nucleus staining DAPI fluorescence).

Figures 18A, 18B, 18C:
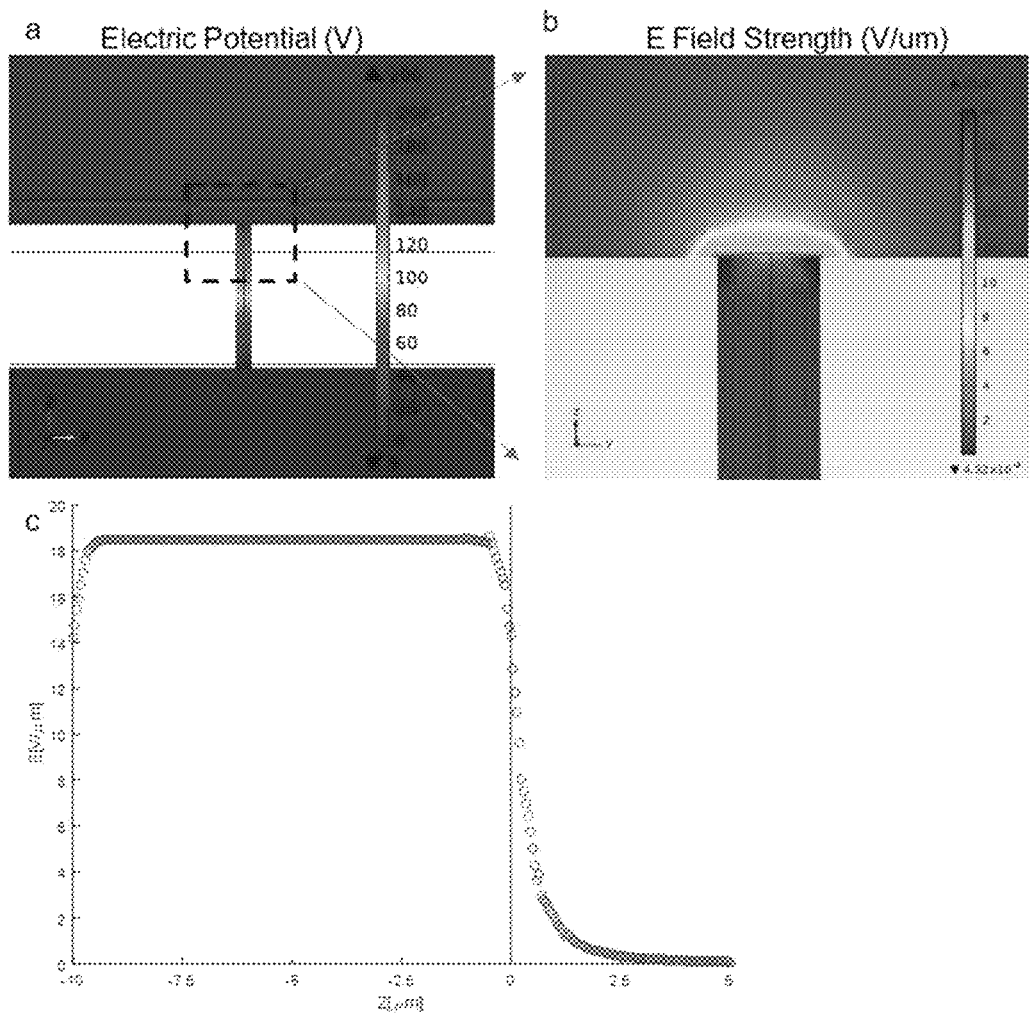
FIGS. 18A-18C show an FEM analysis of the electric field near nanochannel during NEP process (FIG. 18A) the high-resistance nanochannel bears almost all the electric potential drop of applied 200 V voltage pulse for electroporation.

This result can be physically explained by the spatial distribution of the electric field strength in the nanochannel region. The high-resistance nanochannel bears almost all the electric potential drop of applied voltage pulse for electroporation, which was confirmed by the FEM electrostatic simulation result (FIG. 18a). As illustrated in FIG. 18b-c, the electric field strength, which plays a role in the NEP process, nanoporates cell membrane and drives charged biomolecules across the permeable membrane into cytosol via electrophoresis after intensely accelerating them within the nanochannel. This field strength, however, drops sharply once the distance extends away from nanochannel interface (red line drawn in FIG. 18c). Therefore, precise cell positioning against the nanochannel facilitates successful NEP transfection.

To ensure that the cell traps are properly aligned above the nanochannels, one option is to create alignment markers (male and female) in the photo masks for each of the channeling component and the trapping component during the photolithography process. The 2 components can then be aligned using these markers as a reference under the microscope. Since the channeling component and the trapping component are paired when they are defined in the photo mask, once their relative position is fixed, they will be properly aligned.

Figures 19A, 19B, 19C, 19D:
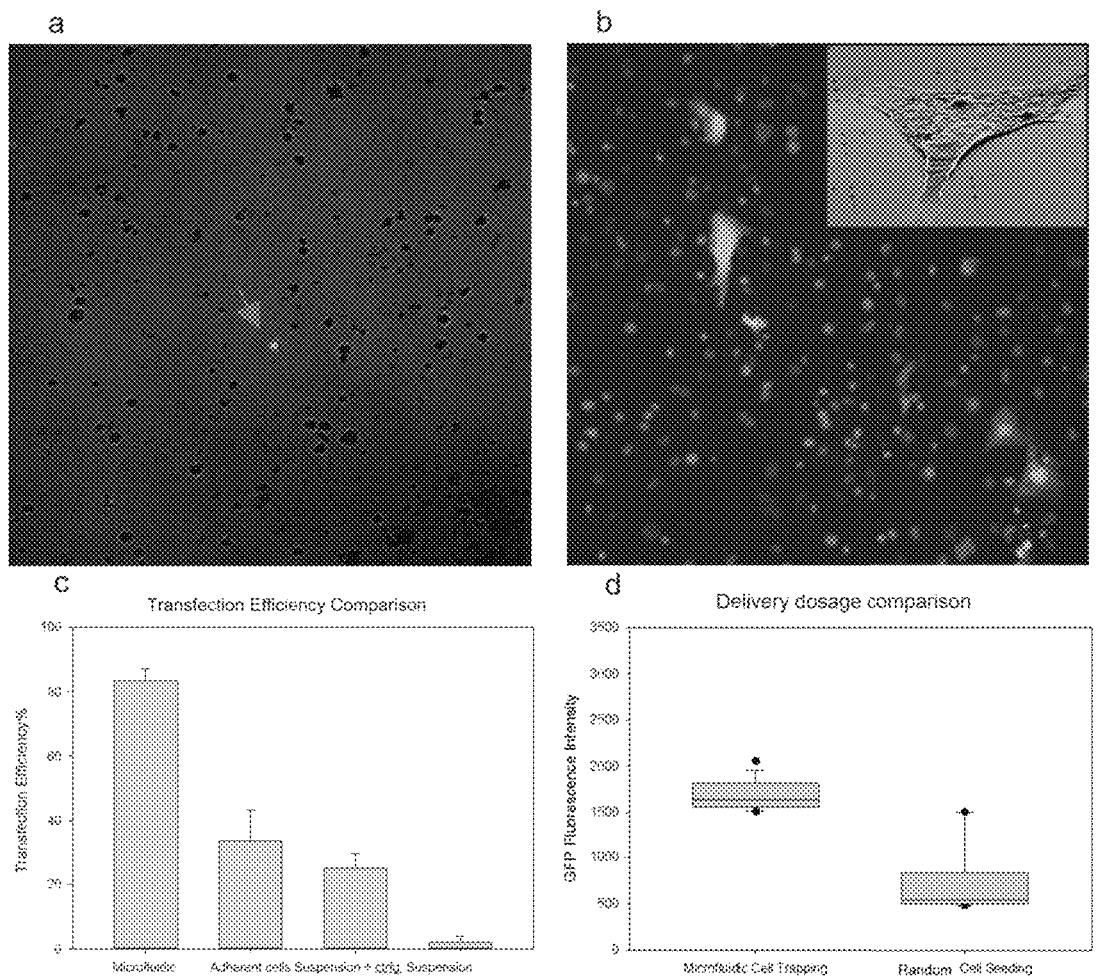
FIGS. 19A-19D demonstrate that the microfluidic cell trapping approach significantly improved NEP-based transfection efficiency.

Example 7: Microfluidic Cell Trapping Significantly Improved NEP-Based Delivery Efficiency and Uniformity The 3D NEP platform described in Chang et al., 2015 and Chang, Bertani et al., 2016 (each of which is incorporated herein by reference) lacked a simple, rapid and efficient massive cell manipulation function, especially for difficult-to-attach suspension cells such as blood cells (e.g., T cells, NK cells, leukemia cells, etc.). As can be seen in FIG. 19a, randomly loaded suspension cells (NK-92, a cancer NK cell line) had low to no transfection efficiency of a PCDH plasmid (7 k bp), as they easily drifted away from the nanochannel surface in the buffer solution without any external forces. Adding a "spin down" step by centrifugation (1000 rpm for 5 min) slightly enhanced the NEP performance and resulted in the transfection efficiency to 25~30% (FIG. 19c). When adherent cells such as fibroblasts were used, close contact between cells and nanochannels can be easily achieved by the cellular anchor behavior. Usually, overnight cell culture of a single layer of cells on the silicon chip surface was done before NEP, so that the cells could attach and spread on the chip surface. By doing so, at least a portion of cells could be in contact with some nanochannels, and thus could be successfully NEP transfected (FIG. 19b). However, this cell attachment process is slow (at least 4-8 h) and completely relies on the cellular behavior which is random and uncontrollable. For example, when mouse embryonic fibroblast (MEF) cells were spread and attached onto the 3D NEP chip surface, some cells would be in contact with one or multiple nanochannels (FIG. 19b, inset) but others might seat in the space between nanochannels. As a result, the number of cells being transfected and the transfection uniformity would depend on the relative position of cells and nanochannels. As shown in FIG. 19c, this method could only achieve 30~40% transfection efficiency even after a prolonged cell anchor processes. To collect the transfected cells from the total cell population, an additional cell sorting step must be conducted, which adds operation difficult and could compromise the cell viability.

Figures 20A, 20B:
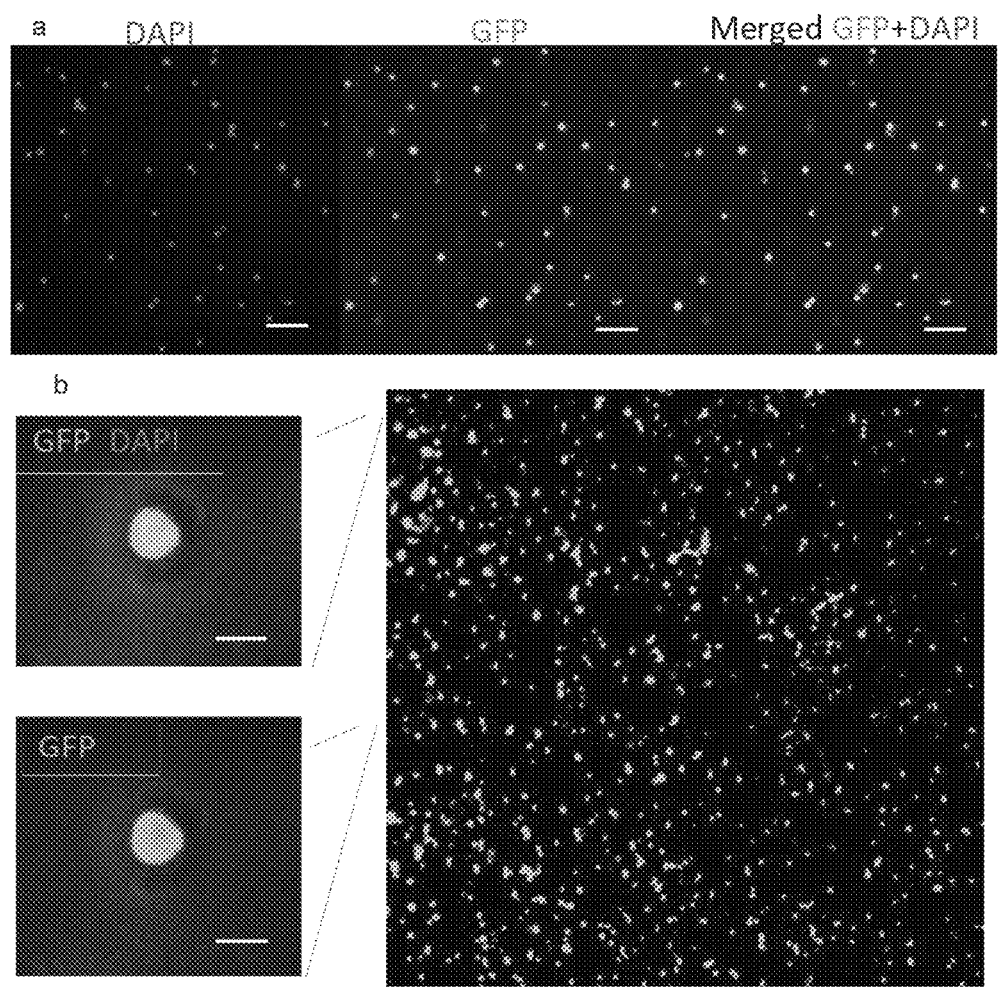
FIGS. 20A-20B show photographs of the NEP-based transfection results with microfluidic cell trapping.

On the other hand, the microfluidic cell trapping method can precisely position individual cells in a large array within 2 min without any cell anchor process, regardless of the cell attachment property. The new method significantly increased the transfection efficiency to >80% (FIG. 19c) by exerting a hydrodynamic "pushing" force on the captured individual cells for NEP-based transfection. Most of the un-transfected cells could be removed simply by flushing them through the microfluidic device because they were not captured by the micro traps. Compared to the centrifugation-based "spin down" random cell loading method, the method also enhanced the delivery dosage and improved the transfection uniformity, as shown in FIG. 19d. The quantified GFP fluorescence intensity distribution in the box plot shows that the microfluidic cell trapping method had a stronger and more uniform YOYO-1 labelled plasmid transfection (FIG. 19(d). Mean fluorescence intensity, representing the delivery dosage jumped from 500 to >1500, with a much smaller scattering of the fluorescent intensity indicating a more uniform delivery across the transfected cell population. Fluorescence micrographs of a living cell array after microfluidic cell trapping followed by uniform cell transfection by NEP is shown in FIG. 20, with delivery cargos including a YOYO™-1-labelled DNA plasmid (~7 kbp) and a FAM-labelled 18-mer oligodeoxynucleotide (ODN, G3139).

Figure 21:
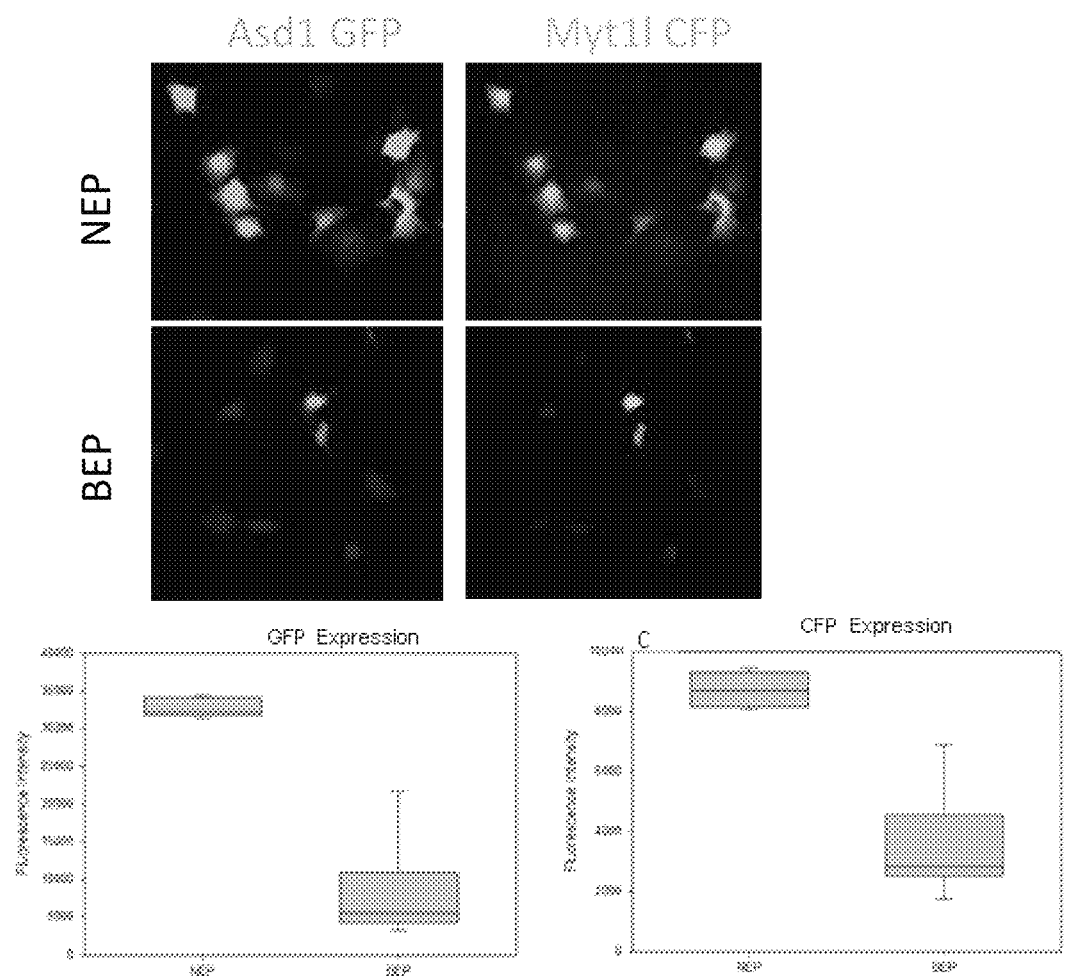
FIG. 21 shows the results of NEP-based transfection of DNA plasmids by microfluidic cell trapping-assisted NEP (microfluidic NEP) in comparison with BEP transfection.

Example 8: Efficient Non-Viral Reprogramming Via Deterministic Transfection Based on Microfluidic Cell Trapping Assisted 3D High-Throughput NEP Platform Cell reprogramming can be performed on either readily available somatic cells (such as skin cells) or induced Pluripotent Stem Cells (iPSCs). Since the dosage of reprogramming factors delivered in individual cell strongly affects the reprogramming pathway, a transfection tool capable of delivering genetic material in a deterministic manner is needed. To demonstrate the potential clinical use of the microfluidic 3D high-throughput NEP platform (microfluidic-NEP, or mNEP), a direct cell reprogramming model relevant to regenerative medicine was tested. Mouse embronic fabroblasts (MEFs) were efficiently co-transfected with DNA plasmids encoding two induced neuron factors: a 7 k by Achaete-Scute Complex Like-1 ((Asch) and a 9 k bp Myelin Transcription Factor 1 Like (Myill) by mNEP, with conventional BEP transfection as comparison. Fluorescent micrographs were captured 24 h after transfection (FIG. 21). Quantification of images showed that the inNEP group had a higher and more uniform average expression level of both Asch11 and Mytl1, indicated by reporter genes. GET intensities from Ascl1 plasmid for NEP was 32,705±1,262 (mean±standard deviation), compared to 8,031±5,914.8 for BEP. CFP intensities from Mytl1 for mNEP was 8,718±561.2 compared to 3,488±1656.6 for BEP.

Example 9: Automating Control of Flow Through the Microfluidic Device

Figure 22:
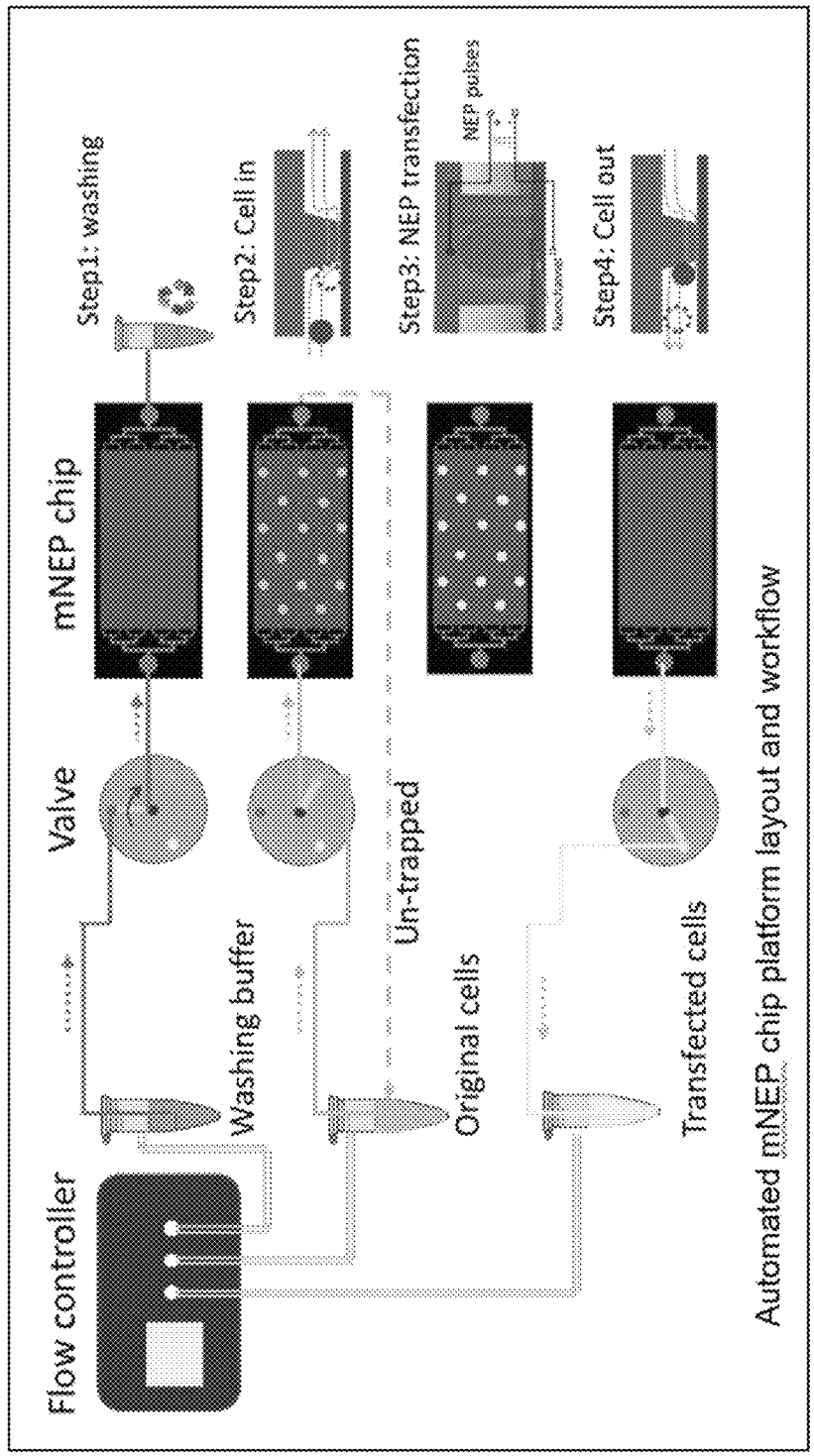
FIG. 22 shows a schematic of an automated method of high throughput cell electroporation. The chip is first washed and wetted by buffer (Step 1). Cells to-be-transfected are then added in from the inlet and flows through the microfluidic channel where individual cells are captured by the microcap traps, ready for electroporation, while the cells that are not trapped will flow through the chip and be collected from the outlet for re-use (Step 2). Once >90% of cell traps are occupied (within 5 min from our experimental results), NEP transfection can be performed by applying electric pulses (200V, 10 ms) across nanochannels (Step 3) under microfluidics. This ensures good cell contact to the nanochannel and minimize Joule heating. After that, the flow direction can be reversed to collect the transfected cells at inlet (Step 4). This cell transfection cycle can be repeated within 10 min We have used FAM-siRNA and GFP plasmids to check the dose control and gene expression respectively of microfluidic NEP (mNEP) for NE transfection. Preliminary results showed that mNEP exhibits much higher NE transfection efficiency than regular NEP.

The mNEP chip is connected to a multi-way bidirectional valve that may automatically control the sequential buffer washing, cell loading, poration, and collection of transfected cells cycle with a digital flow controller. In each cell transfection cycle, as shown in the work flow in FIG. 22, the chip is first washed and wetted by buffer (Step 1). Cells to-be-transfected are then added in from the inlet and flows through the microfluidic channel where individual cells are captured by the microcap traps, ready for electroporation, while the cells that are not trapped will flow through the chip and be collected from the outlet for re-use (Step 2). Once >90% of cell traps are occupied (within 5 min from our experimental results), NEP transfection can be performed by applying electric pulses (200V, 10 ms) across nanochannels (Step 3) under microfluidics. This ensures good cell contact to the nanochannel and minimize Joule heating. After that, the flow direction can be reversed to collect the transfected cells at inlet (Step 4). This cell transfection cycle can be repeated within 10 min.

Example 10: Microfluidic NEP can Quickly and Effectively Load Biological Drugs in Neutrophils (NE) for Treatment of Severe Inflammatory Diseases Neutrophils (NEs) are the most abundant immune cells which are known to target and penetrate inflamed and infected tissues in vivo. Unlike synthetic nanocarriers that often accumulate in liver, spleen and kidney, or identify the disease site based on either the enhanced permeability and retention effect, or ligand-receptor interactions, NEs are activated by the inflammatory cytokine signals, such as IL-6, IL-8, TNF-α and CXCL1/KC to reach the target tissue and migrate across endothelial cells of the monolayer barrier in lumen of blood vessels. For severe inflammatory diseases such as SLE, NEs are ideal carriers if biological drugs can be pre-loaded because NEs may release their therapeutic cargo at the inflammatory sites on excessive activation by concentrated inflammatory cytokines in the form of neutrophil extracellular traps (NETs). Ex vivo delivery of drug-containing NEs, however, requires fast cell transfection because NEs have a <24 h life span in vitro. Moreover, loading high number of nucleic acid copies with precise compositions (in the case of multi-nucleic acid therapy) in NEs is also essential.

Figures 23A, 23B, 23C:
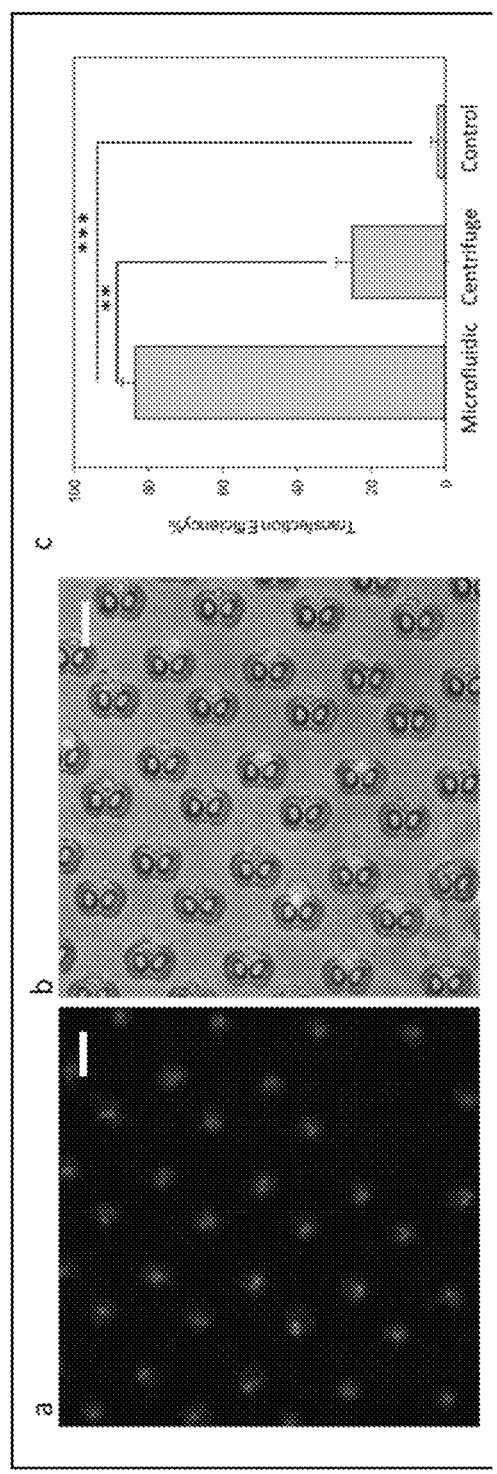
FIGS. 23A-23C show the results of NEs FAM-ODN transfection by mNEP.
Figure 24:
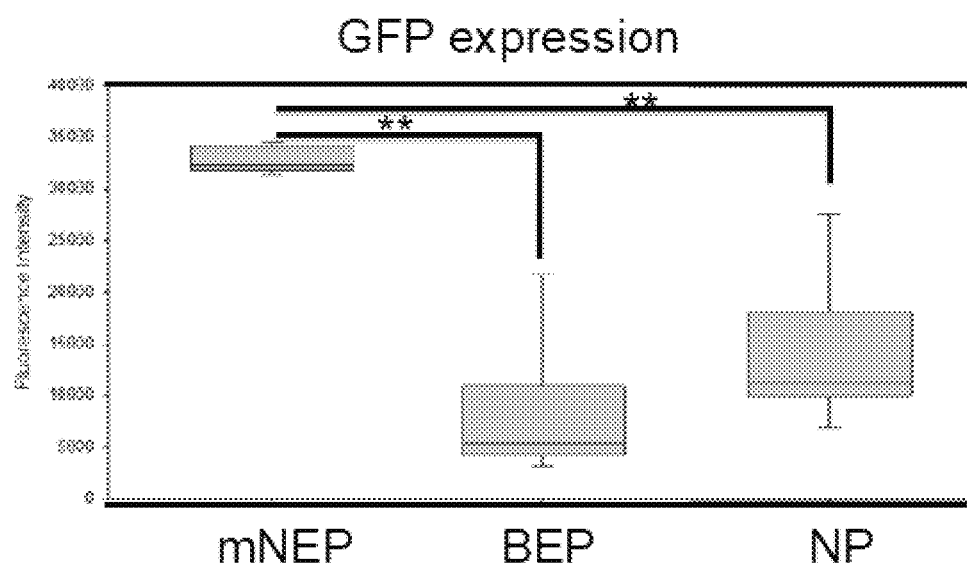
FIG. 24 shows the biological variation of GFP plasmid transfection by mNEP, BEP and Nanoparticle (NP). **p<0.01, t-test.

In this example, FAM-siRNA and GFP plasmids are used to check the dose control and gene expression respectively of mNEP for NE transfection. Preliminary results showed that microfluidic NEP exhibits much higher NE transfection efficiency than NEP using the random loading or centrifugation methods described above in Example 7 (FIGS. 23A-23C) and lower biological variation than BEP and liposomal nanoparticles (NP) with superior GFP expression uniformity in transfected cells (FIG. 24).

While the invention has been described with reference to particular embodiments and implementations, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular implementations disclosed herein, but that the invention will include all implementations falling within the scope of the appended claims.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated.

REFERENCES

Boukany, P. E., Morss, A., Liao, W. C., Henslee, B., Jung, H., Zhang, X., . . . Lee, L. J. (2011). Nanochannel electroporation delivers precise amounts of biomolecules into living cells. *Nat Nanotechnol*, 6(11), 747-754. doi: 10.1038/nnano.2011.164

Chang, L., Bertani, P., Gallego-Perez, D., Yang, Z., Chen, F., Chiang, C., . . . Lu, W. (2016). 3D nanochannel electroporation for high-throughput cell transfection with high uniformity and dosage control. *Nanoscale*, 8(1), 243-252. doi:10.1039/c5nr03187g Chang, L., Gallego-Perez, D., Chiang, C. L., Bertani, P., Kuang, T., Sheng, Y., . . . Lee, L. J. (2016). Controllable Large-Scale Transfection of Primary Mammalian Cardiomyocytes on a Nanochannel Array Platform. *Small*, 12(43), 5971-5980. doi:10.1002/smll.201601465

Chang, L., Gallego-Perez, D., Zhao, X., Bertani, P., Yang, Z., Chiang, C. L., . . . Lee, L. J. (2015). Dielectrophoresis-assisted 3D nanoelectroporation for non-viral cell transfection in adoptive immunotherapy. *Lab Chip*, 15(15), 3147-3153. doi:10.1039/c51c00553 a Chang, L., Howdyshell, M., Liao, W. C., Chiang, C. L., Gallego-Perez, D., Yang, Z., . . . Sooryakumar, R. (2015). Magnetic tweezers-based 3D microchannel electroporation for high-throughput gene transfection in living cells. *Small*, 11(15), 1818-1828. doi:10.1002/smll.201402564

Di Carlo, D., Aghdam, N., & Lee, L. P. (2006). Single-cell enzyme concentrations, kinetics, and inhibition analysis using high-density hydrodynamic cell isolation arrays. *Anal Chem*, 78(14), 4925-4930. doi:10.1021/ac060541s Skelley, A. M., Kirak, O., Suh, H., Jaenisch, R., & Voldman, J. (2009). Microfluidic control of cell pairing and fusion. *Nat Methods*, 6(2), 147-152. doi:10.1038/nmeth.1290

Zhang, K., Chou, C. K., Xia, X., Hung, M. C., & Qin, L. (2014). Block-Cell-Printing for live single-cell printing. *Proc Natl Acad Sci USA*, 111(8), 2948-2953. doi:10.1073/pnas.1313661111

What is claimed is:

1. A microfluidic device for high throughput cell electroporation, the device comprising:
    a trapping component at least partially defining an upper boundary of a fluidic chamber and comprising a cell trap array, wherein a plurality of cell traps of the cell trap array extend downward into the fluidic chamber;
    a channeling component positioned beneath the trapping component and at least partially defining a lower boundary of the fluidic chamber, the channeling component comprising a nanochannel array in fluid communication with and extending downward from the fluidic chamber, wherein a plurality of the nanochannels of the nanochannel array have an opening that is positioned in vertical alignment with a different cell trap of the cell trap array; and
    an upper electrode layer and a lower electrode layer configured to generate an electric field within the fluidic chamber.

2. The microfluidic device of claim 1, further comprising a reservoir positioned beneath the channeling component, wherein the upper boundary of the reservoir is at least partially defined by the channeling component such that the reservoir is in fluid communication with the fluidic chamber.

3. The microfluidic device of claim 2, wherein the lower boundary of the reservoir is at least partially defined by the lower electrode.

4. The microfluidic device of claim 2, wherein the side boundaries of the reservoir are at least partially defined by a spacing material.

5. The microfluidic device of claim 1, wherein at least one nanochannel of the nanochannel array has a height of from 1 micrometer to 20 micrometers.

6. The microfluidic device of claim 1, wherein at least one nanochannel of the nanochannel array has a diameter of from 1 nanometer to 999 nanometers.

7. The microfluidic device of claim 1, wherein the channeling component further comprises a plurality of microchannels extending upward from a lower surface, each microchannel in fluid communication with multiple nanochannels of the nanochannel array.

8. The microfluidic device of claim 1, further comprising a space between the lower edge of each cell trap and the channeling component.

9. The microfluidic device of claim 1, wherein each cell trap of the cell trap array comprises a cupping region partially defined by walls of the cell trap, the cupping region comprising an entry portion oriented toward an inlet side of the fluidic chamber.

10. The microfluidic device of claim 9, wherein the plurality of nanochannels of the nanochannel array are each positioned vertically beneath the cupping region of a cell trap.

11. The microfluidic device of claim 1, wherein the upper electrode layer is positioned on a lower surface of the trapping component and in fluid communication with the fluidic chamber.

12. The microfluidic device of claim 1, wherein the lower electrode is positioned beneath the channeling component and in fluid communication with the fluidic chamber.

13. The microfluidic device of claim 1, wherein at least one cell trap of the cell trap array comprises a fluid exit gap.

14. A method of performing high throughput cell electroporation, the method comprising:
    flowing a cell suspension in a forward direction through an inlet and into the fluidic chamber of the microfluidic device of claim 1;
    trapping a plurality of cells within the array of cell traps;
    continuing a forward flow of fluid from the inlet of the fluidic chamber to an outlet of the fluidic chamber, thereby creating fluidic patterns around the cell traps that position at least a portion of the trapped cells into secure contact with the nanochannels;
    electroporating the portion of the trapped cells that are in secure contact with the nanochannels to produce electroporated cells;
    releasing the electroporated cells from the cell traps; and
    collecting the electroporated cells.

15. The method of claim 14, wherein flowing cells in a forward direction through the inlet comprises flowing a cell suspension having a cell density of from 3 million cells/mL to 15 million cells/mL.

16. The method of claim 14, wherein flowing cells in a forward direction through an inlet comprises flowing a cell suspension at an inlet flow velocity of from 70 to 130 microns per second.

17. The method of claim 14, wherein creating fluidic patterns around the cell traps comprises stopping flow within a cupping region of the cell trap or slowing flow within the cupping region to no more than 20% of the inlet flow velocity.

18. The method of claim 14, further comprising transfecting at least some of the portion of trapped cells with at least one of genetic material, drugs, proteins, molecular probes, nanoparticles, and sensors during electroporation.

19. The method of claim 18, wherein at least some of the portion of trapped cells is transfected with genetic material up to 100,000 base pairs in size.

20. The method of claim 14, wherein electroporating the portion of trapped cells comprises generating an electric field within and immediately adjacent to each nanochannel.

21. The method of claim 20, wherein each nanochannel has a nanochannel diameter at the boundary of the microfluidic chamber, a nanochannel electric field is measured at a depth beneath the boundary of the microfluidic chamber that is equivalent to the nanochannel diameter, and wherein within the microfluidic chamber, at a lateral distance away from a side of the nanochannel that is equivalent to the nanochannel diameter, the strength of the electric field is less than 20% the strength of the electric field within the nanochannel.

22. The method of claim 14, wherein, for time periods greater than 10 minutes, the rate of cell electroporation is greater than 1,000 cells per minute per square centimeter of microfluidic chamber.

23. The method of claim 14, wherein releasing the cells from the cell traps comprises slowing or stopping the forward flow of fluid.

24. The method of claim 14, further comprising reversing the direction of fluid flow within the microfluidic device to release and collect the electroporated cells.

25. A microfluidic device for high throughput cell electroporation, the device comprising:

a trapping component at least partially defining an upper boundary of a fluidic chamber and comprising a cell trap array, wherein a plurality of cell traps of the cell trap array extend downward into the fluidic chamber;

a channeling component positioned beneath the trapping component and at least partially defining a lower boundary of the fluidic chamber, the channeling component comprising a nanochannel array in fluid communication with and extending downward from the fluidic chamber, wherein a plurality of the nanochannels of the nanochannel array are positioned in vertical alignment with a plurality of cell traps of the cell trap array; and an upper electrode layer and a lower electrode layer configured to generate an electric field within the fluidic chamber.

26. The microfluidic device of claim 25, wherein at least one cell trap of the cell trap array comprises a fluid exit gap.

* * * * *